United States Patent
McKearin et al.

(10) Patent No.: US 11,878,994 B1
(45) Date of Patent: Jan. 23, 2024

(54) COMPOSITIONS FOR TREATMENT OF INFLAMMATION

(71) Applicant: Metro International Biotech, LLC, Worcester, MA (US)

(72) Inventors: James M. McKearin, Worcester, MA (US); David J. Livingston, Worcester, MA (US); Karen Lavery, Worcester, MA (US)

(73) Assignee: Metro International Biotech, LLC, Worcester, MA (US)

( * ) Notice: Subject to any disclaimer, the term of this patent is extended or adjusted under 35 U.S.C. 154(b) by 0 days.

(21) Appl. No.: 18/368,257

(22) Filed: Sep. 14, 2023

Related U.S. Application Data

(63) Continuation of application No. PCT/US2022/053680, filed on Dec. 21, 2022.

(60) Provisional application No. 63/292,672, filed on Dec. 22, 2021.

(51) Int. Cl.
*C07H 19/23* (2006.01)

(52) U.S. Cl.
CPC .................................. *C07H 19/23* (2013.01)

(58) Field of Classification Search
None
See application file for complete search history.

(56) References Cited

U.S. PATENT DOCUMENTS

| | | |
|---|---|---|
| 2020/0181188 A1 | 6/2020 | Rhonemus et al. |
| 2020/0352966 A1 | 11/2020 | Normington et al. |
| 2021/0214386 A1 | 7/2021 | Sauve |

OTHER PUBLICATIONS

International Search Report and Written Opinion for Application No. PCT/US22/53680 dated Apr. 7, 2023.

Mehellou et al., "The ProTide Prodrug Technology: From the Concept to the Clinic," Journal of Medicinal Chemistry, 61: 2211-2226 (2018).

National Center for Biotechnology Information)"3-(3,7-Dimethyl-2,6-dioxopurin-l-yl)propyl 1-oxidopyridin-1-ium-4-carboxylate: PUBCHEM CID 8791842" Pubchem entry (online), pp. 1-7, Jul. 30, 2006; Retrieved on Feb. 18, 2023 from the Internet: [URL: https://pubchem.ncbi.nlm.nih.gov/compound/8791842]; p. 2.

National Center for Biotechnology Information)"1-[3,4-Dihydroxy-5-(phosphonooxymethyl)oxolan-2-yl]pyridin-l-lum-3-carboxylic acid: PUBCHEM CID 941" Pubchem entry (online), pp. 1-11, Mar. 25, 2005; Retrieved on Feb. 18, 2023 from the Internet: [URL: https://pubchem.ncbi.nlm.nih.gov/compound/941]; p. 2.

National Center for Biotechnology Information) "5-(3-Carbamoylpyridin-1-ium-1-yl}-3,4-dihydroxyoxolan-2-yl]methyl dihydrogen phosphate: PUBCHEM CID 939" Pubchem entry (online), pp. 1-9, Mar. 25, 2005; Retrieved on Feb. 18, 2023 from the Internet: [URL: https://pubchem.ncbi.nlm.nih.gov/compound/939]; p. 2.

National Center for Biotechnology Information) "3-methyl-1-(pyridine-3-carbonyl)-7H-purine-2,6-dione: PUBCHEM CID 129249540" Pubchem entry (online), pp. 1-8, Aug. 4, 2017; Retrieved on Feb. 19, 2023 from the Internet: [URL: https://pubchem.ncbi.nlm.nih.gov/compound/129249540]; p. 2.

*Primary Examiner* — Dale R Miller

(74) *Attorney, Agent, or Firm* — Foley Hoag LLP; David P. J. Halstead D.; Benjamin A. Vaughan

(57) ABSTRACT

Disclosed herein are novel compositions and methods for the treatment of inflammation. Also described herein are methods for the identification of agents useful in the foregoing methods. The invention relates to methods for treatment and prevention of disorders associated with inflammation by administering agents that may also increase levels of NAD+, such as NAD+ precursors or agents involved in NAD+ biosynthesis.

30 Claims, 2 Drawing Sheets

COMPOSITIONS FOR TREATMENT OF INFLAMMATION

RELATED APPLICATIONS

This application is a continuation of International Application No. PCT/US22/53680, filed on Dec. 21, 2022, which claims priority to U.S. Provisional Application 63/292,672, filed Dec. 22, 2021, each of which are incorporated herein by reference in their entirety for all purposes.

BACKGROUND

Nicotinamide Adenine Dinucleotide (NAD) is an essential metabolic cofactor. Recent research has indicated that NAD levels decline with age and in certain mammalian disease states, and that therapeutically increasing NAD levels has health benefits. However, NAD is an intracellular metabolite, and does not readily lend itself to external supplementation. It has been suggested that utilizing precursors to the natural synthesis of NAD may be an effective way to increase NAD.

Two exemplary precursors that could be administered to increase NAD are nicotinamide mononucleotide (NMN), which is directly synthesized into NAD, and nicotinamide riboside (NR), which is recycled from the utilization of NAD, into NMN. There are no known dietary or environmental sources of NMN or NR. Accordingly, in order to use these precursors as drugs or supplements, they must be manufactured.

Nicotinamide adenine dinucleotide (NAD) boosting compounds, such as (3-Nicotinamide mononucleotide (NMN), have recently gained attention for use in the treatment, amelioration, mitigation, slowing, arrest, prevention and/or reversal of a wide variety of diseases and conditions, including but not limited to age-associated degenerative changes, such as age-related obesity, age-related increases in blood lipid levels, age-related decreases in insulin sensitivity, age-related decreases in memory function, and age-related changes in eye function, such as macular degeneration.

SUMMARY

Disclosed herein are compounds including a xanthine moiety, or an analogue of a xanthine moiety, and additional moieties provided for administration for treatment of inflammation, among other indications.

In some embodiments, the present disclosure relates to a compound having a structure represented by Formula (I):

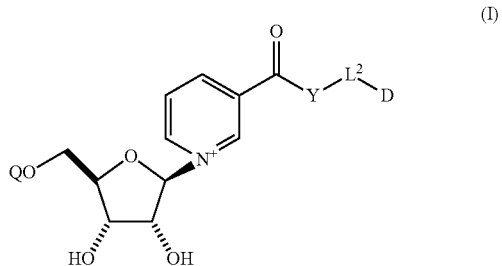

or a pharmaceutically acceptable salt thereof, wherein
Q is H or a phosphate group (—PO(OH)$_2$ or —PO(OH)(O$^-$)),
Y is —NH— or —O—, and
L$^2$ is (C1-6)alkylene or

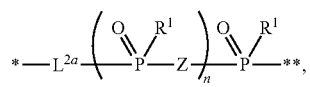

wherein L$^{2a}$ is alkylene; each R$^1$ is independently OH, O$^-$, O-alkyl, NH-alkyl, or alkyl; Z is O or NH; n is 0 or 1; * is the point of attachment to the oxygen atom; and ** is the point of attachment to D, or
Y and L$^2$ are absent; and
D is an optionally substituted xanthine.

In various embodiments, the chemical variables are as further defined herein.

In various embodiments, the present disclosure relates to a pharmaceutically acceptable salt of a compound of any one of the preceding clauses, wherein the salt comprises a cation selected from H$^+$, Li$^+$, Na$^+$, K$^+$, Mg$^{2+}$, and Ca$^{2+}$. In various embodiments, the present disclosure relates to a pharmaceutically acceptable salt of a compound of any one of the preceding clauses, wherein the salt comprises an anion selected from acetate, triflate, halide, trifluoroacetate, formate, H$_2$PO$_4^-$, HPO$_4^{2-}$, OH$^-$, HSO$_4^-$, SO$_4^{2-}$, NO$_3^-$, HCO$_3^-$, and CO$_3^{2-}$.

Also disclosed herein are pharmaceutical compositions comprising a compound or pharmaceutically acceptable salt of any one of the preceding clauses and one or more pharmaceutically acceptable excipients. In various embodiments, the pharmaceutically acceptable excipient is selected from an anti-adherent, a binder, a coating, a dye, a disintegrant, a flavoring agent, a glidant, a lubricant, a preservative, a sorbent, a sweetener, a dispersant, a diluent, a filler, a granulating agent, a coating agent, a wax, a suspending agent, a wetting agent, a vehicle, a liquid carrier, and combinations thereof.

In various embodiments, the composition is in a solid form selected from a tablet, a pill, a capsule, a caplet, a troche, granules, powders, a sachet, a dry powder inhalation form, a chewable, a pastille, and a lozenge. Further described herein are pharmaceutical compositions of any one of the above clauses, wherein one or more of the compounds and pharmaceutically acceptable salts are present in the composition in an amount from about 0.001% by weight to about 90% by weight.

Also disclosed herein are various methods of treatment, including a method of treating inflammation in a subject in need thereof, said method comprising administering a compound or pharmaceutically acceptable salt of any one of the above clauses, or a pharmaceutical composition of any one of the above clauses, to the subject. In various embodiments, the inflammation is mediated by a phosphodiesterase. In various embodiments, the inflammation is related to asthma, chronic obstructive pulmonary disease (COPD), psoriasis, atopic dermatitis, inflammatory bowel disease (IBD), rheumatoid arthritis (RA), lupus, acute kidney injury (AKI), chronic kidney disease, or neuroinflammation. Also disclosed herein are methods of treatment of acute kidney injury in a subject, said method comprising administering a compound or pharmaceutically acceptable salt of any one of the above clauses, or a pharmaceutical composition of any one of the above clauses, to the subject. Also disclosed herein are methods of treatment for increasing NAD+ in a subject, said method comprising administering a compound or pharmaceutically acceptable salt of any one of the above clauses, or a pharmaceutical composition of any one of the above clauses, to the subject. In various methods of treatment, the compound, the pharmaceutically acceptable salt, and/or the pharmaceutical composition is administered orally. In various embodiments, the oral administration occurs in an outpatient setting. In various embodiments, the subject performs the oral administration.

In some embodiments said compound is administered in a dose of between about 100 mg and about 4 grams per day. In some embodiments said compound is administered in a dose between about 500 mg and about 2 grams per day. In some embodiments said compound is administered in a daily dosage regimen selected from once daily, twice daily, three times daily, and four times daily. In some embodiments said compound is administered for a period up to 5 days inclusive. In some embodiments said compound is administered for a period greater than 5 days.

Columns 1-4 Controls: 1) No inhibitor, 2) water, 3) RLPM 60 micromolar, 4) IBMX micromolar.

Columns 5-11 at 0.6 mM: 5) theophylline, 6) caffeine, 7) comparative compound, 8) NRCl, 9) Compound 3, 10) Compound 1, 11) Compound 6.

Columns 12-18 at 6 mM: 12) theophylline, 13) caffeine, 14) comparative compound, NRCl, 16) Compound 3, 17) Compound 1, 18) Compound 6.

Figure 2:
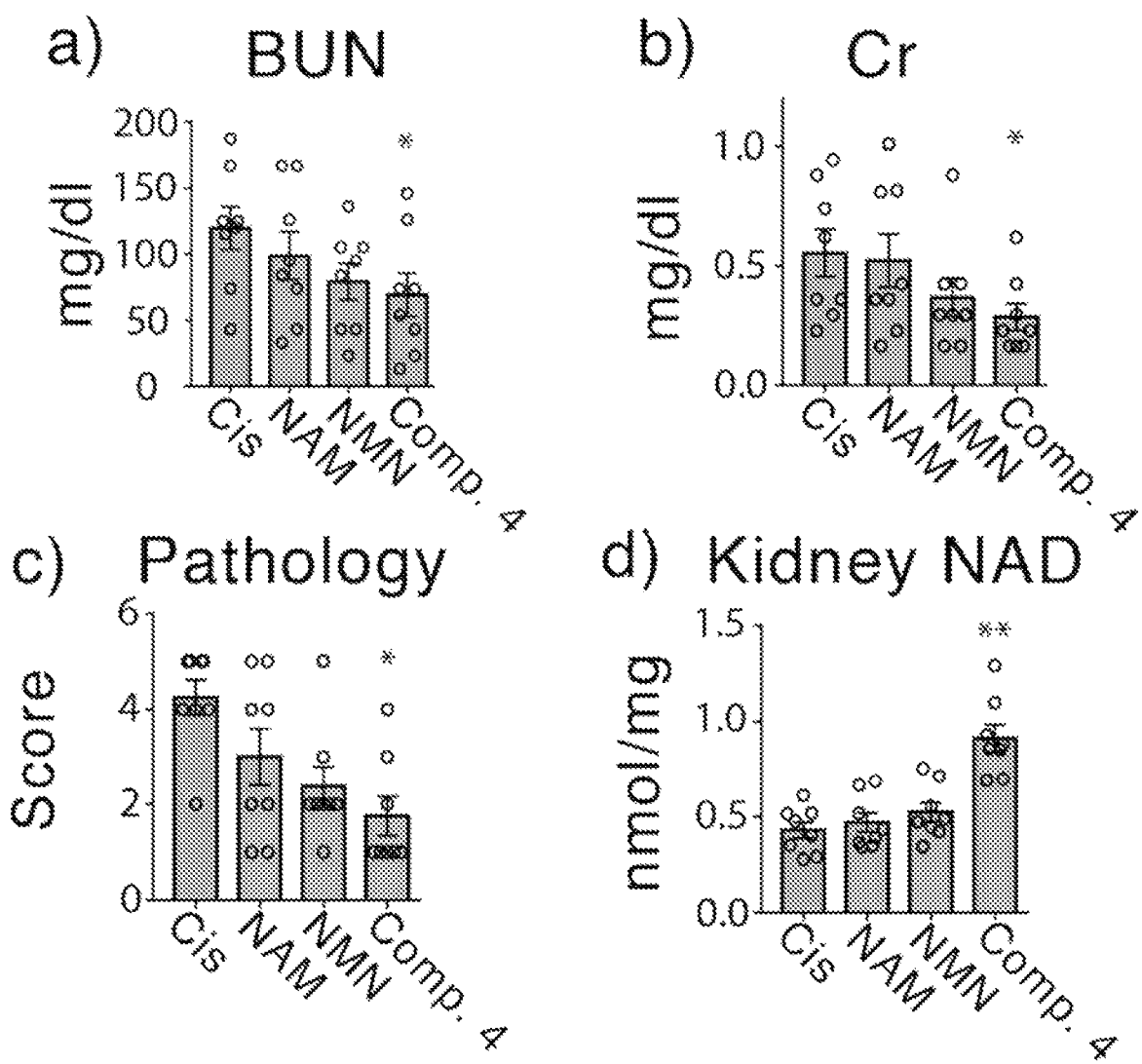

FIG. 2 provides results from a cisplatin-induced model of acute kidney injury (AKI) as fully described in Example B2. Readouts from the testing were (a) biliary urinary nitrogen (BUN), (b) serum creatinine (Cr), (c) histopathology of kidney sections viewed and graded for tubular necrosis, and (d) NAD concentration in the kidney. In each of (a)-(d), Column 1 was cisplatin alone, Column 2 was niacinamide (Nam), Column 3 was nicotinamide mononucleotide (NMN), and Column 4 was Compound 4.

DETAILED DESCRIPTION

Definitions

Unless defined otherwise, all technical and scientific terms used herein have the meaning commonly understood by a person skilled in the art of the present disclosure. As used herein, the following terms have the meanings ascribed to them below, unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "purified," as described herein, refers to the purity of a given compound. For example, a compound is "purified" when the given compound is a major component of the composition, i.e., at least about 50% w/w pure. Thus, "purified" embraces at least about 50% w/w purity, at least about 60% w/w purity, at least about 70% purity, at least about 80% purity, at least about 85% purity, at least about 90% purity, at least about 92% purity, at least about 94% purity, at least about 96% purity, at least about 97% purity, at least about 98% purity, at least about 99% purity, at least about 99.5% purity, and at least about 99.9% purity, wherein "substantially pure" embraces at least about 97% purity, at least about 98% purity, at least about 99% purity, at least about 99.5% purity, and at least about 99.9% purity.

The term "metabolite," as described herein, refers to a compound produced in vivo after administration to a subject.

The term "salts," as described herein, refers to a compound comprising a cation and an anion, which can be produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $Mg^{2+}$, $Ca_{2+}$, $NH_gR_{4-g}^+$, in which R is a $C_{1-3}$ alkyl and g is a number selected from 0, 1, 2, 3, or 4. It should be understood that all references to pharmaceutically acceptable salts include solvent addition forms (solvates) or crystal forms (polymorphs) as defined herein, of the same acid addition salt.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta-etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

The term "minimum effective dose" (MED) as used herein refers to the lowest dose level of a pharmaceutical product that provides a clinically significant response in average efficacy, which is also statistically significantly superior to the response provided by the placebo.

The term "institutional review board" or "IRB" as used herein refers to a type of committee that applies research ethics by reviewing the methods proposed for research to ensure that they are ethical.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

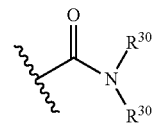

wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

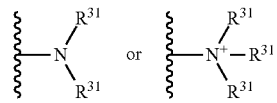

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

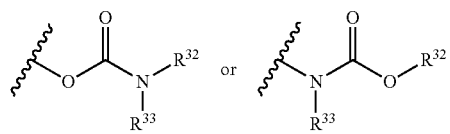

wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{34}$, wherein $R^{34}$ represents a hydrocarbyl group.

The term "carboxy", as used herein, refers to a group represented by the formula —$CO_2H$.

The term "ester", as used herein, refers to a group —C(O)$OR^{35}$ wherein $R^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

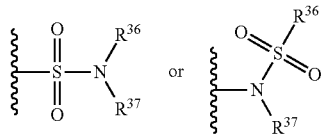

wherein R$^{36}$ and R$^{37}$ independently represent hydrogen or hydrocarbyl, such as alkyl, or R$^{36}$ and R$^{37}$ taken together with the intervening atom(s) complete a heterocycle having from 4 to 8 atoms in the ring structure.

The term "sulfoxide" is art-recognized and refers to the group —S(O)—R$^{38}$, wherein R$^{38}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{39}$, wherein R$^{39}$ represents a hydrocarbyl.

The term "thioalkyl", as used herein, refers to an alkyl group substituted with a thiol group.

The term "thioester", as used herein, refers to a group —C(O)SR$^{40}$ or —SC(O)R$^{40}$ wherein R$^{10}$ represents a hydrocarbyl.

The term "thioether", as used herein, is equivalent to an ether, wherein the oxygen is replaced with a sulfur.

By "xanthine" is meant a moiety corresponding to the following ring structure where R$^1$, R$^2$ and R$^3$ are each hydrogen. A "substituted xanthine" is a compound with the below xanthine bicyclic core and various substituents at any or all of the R$^1$, R$^2$ and R$^3$ positions, including the various non-limiting substitution patterns as follows:

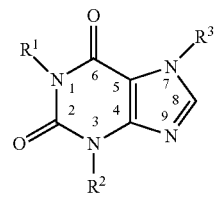

| Name | R$^1$ | R$^2$ | R$^3$ |
|---|---|---|---|
| Xanthine | H | H | H |
| Caffeine | CH$_3$ | CH$_3$ | CH$_3$ |
| Theophylline | CH$_3$ | CH$_3$ | H |
| Theobromine | H | CH$_3$ | CH$_3$ |
| Paraxanthine | CH$_3$ | H | CH$_3$ |

Disclosed herein are compounds having a structure represented by Formula (I):

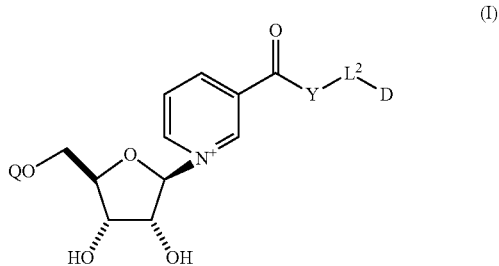

(I)

or a pharmaceutically acceptable salt thereof, wherein
Q is H or a phosphate group (—PO(OH)$_2$ or —PO(OH)(O$^-$)),
Y is —NH— or —O—, and
L$^2$ is (C1-6)alkylene or

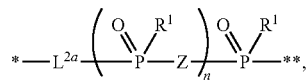

wherein $L^{2a}$ is alkylene; each $R^1$ is independently OH, O⁻, O-alkyl, NH-alkyl, or alkyl; Z is O or NH; n is 0 or 1; * is the point of attachment to the oxygen atom; and ** is the point of attachment to D, or Y and $L^2$ are absent; and D is an optionally substituted xanthine.

In certain embodiments, Y is —O—. In other embodiments, Y is —HN—. In certain embodiments, $L^{2a}$ is (C1-3)alkylene. In other embodiments, $L^{2a}$ is C3 alkylene. In some embodiments, each $R^1$ is OH or O⁻. In certain embodiments, each Z is O. In some embodiments, n is 1. In other embodiments, n is 0. In certain embodiments, Y and $L^2$ are absent. In other embodiments, $L^2$ is (C1-6)alkylene or (C1-3)alkylene.

Disclosed herein are compounds having a structure represented by Formula (II):

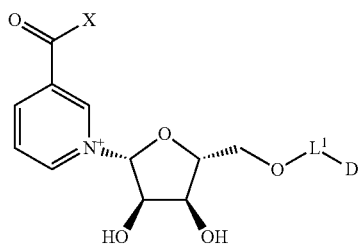

(II)

or a pharmaceutically acceptable salt thereof, wherein

X is $NH_2$ or OH or O⁻;

$L^1$ is

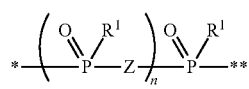

wherein each $R^1$ is independently OH, O⁻, O-alkyl, NH-alkyl, or alkyl; Z is O or NH; n is 0 or 1; * is the point of attachment to the oxygen atom; and ** is the point of attachment to D; and D is an optionally substituted xanthine.

In certain embodiments, X is OH or O⁻. In other embodiments, X is $NH_2$. In some embodiments, each $R^1$ is OH or O⁻. In certain embodiments, each Z is O. In some embodiments, n is 1. In other embodiments, n is 0. In certain embodiments, D is an anti-inflammatory drug. In other embodiments, D is a substituted xanthine. In some embodiments, D is a methylxanthine. In certain embodiments, the methylxanthine is caffeine, theobromine, or theophylline, such as theobromine.

In some embodiments, D is attached at position 1 of the xanthine ring to $L^1$ or $L^2$. In other embodiments, D is attached at position 3 of the xanthine ring to $L^1$ or $L^2$. In some embodiments, D is attached at position 7 of the xanthine ring to $L^1$ or $L^2$.

In certain embodiments, D is represented by Formula (III):

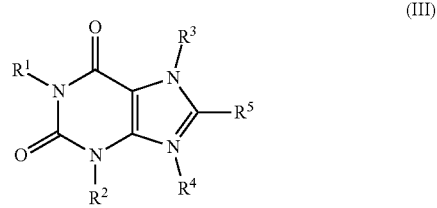

(III)

wherein each $R^1$, $R^2$, $R^3$, and $R^4$ is independently H, (C1-6)alkyl, (C2-6)alkenyl, (C2-6)alkynyl, (C3-7)cycloalkyl, aryl, heteroaryl, —C(=O)(C1-6)alkyl, C(=O)(O)(C1-6)alkyl, absent, or the point of attachment to L, provided that one of $R^1$, $R^2$, $R^3$, and $R^4$ is the point of attachment; and further provided that when $R^4$ is not absent or is the point of attachment to L, the nitrogen to which it is attached bears a positive charge;

$R^5$ is H, (C1-6)alkyl, (C2-6)alkenyl, (C2-6)alkynyl, (C3-7)cycloalkyl, aryl, heteroaryl, or $NR^6R^7$; and each $R^6$ and $R^7$ is independently H, (C1-6)alkyl, (C2-6)alkenyl, (C2-6)alkynyl, or aryl.

In certain embodiments, each $R^1$ and $R^3$ is independently (C1-6)alkyl, (C2-6)alkenyl, (C2-6)alkynyl, (C3-7)cycloalkyl, aryl, heteroaryl, —C(=O)(C1-6)alkyl, C(=O)(0)(C1-6)alkyl, or the point of attachment to L. In other embodiments, each $R^2$, and $R^3$ is independently (C1-6)alkyl, (C2-6)alkenyl, (C2-6)alkynyl, (C3-7)cycloalkyl, aryl, heteroaryl, —C(=O)(C1-6)alkyl, C(=O)(O)(C1-6)alkyl, or the point of attachment.

In certain embodiments, each $R^1$, $R^2$, $R^3$, and $R^4$ is independently H, (C1-6)alkyl, or absent. In other embodiments, at least one of $R^2$, $R^3$, and $R^4$ is (C1-6)alkyl. In some embodiments, at least one of $R^1$, $R^2$, $R^3$, and $R^4$ is (C1-6) alkyl substituted with —$C(O)CH_3$. In certain embodiments, at least one of $R^1$, $R^2$, $R^3$, and $R^4$ is methyl.

In some embodiments, $R^4$ is H or absent. In certain embodiments, $R^5$ is H or (C1-6)alkyl. In certain embodiments, $R^5$ is H. In some embodiments, $R^1$ is the point of attachment to L. In other embodiments, $R^1$ is the point of attachment to L 2 or $L^1$, $R^2$ is $CH_3$, $R^3$ is $CH_3$, $R^4$ is absent, and $R^5$ is H.

Disclosed herein are compounds having the structure of one of the following:

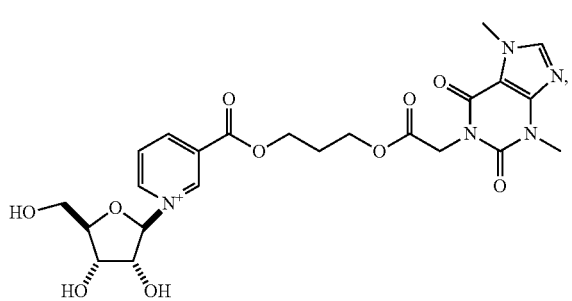

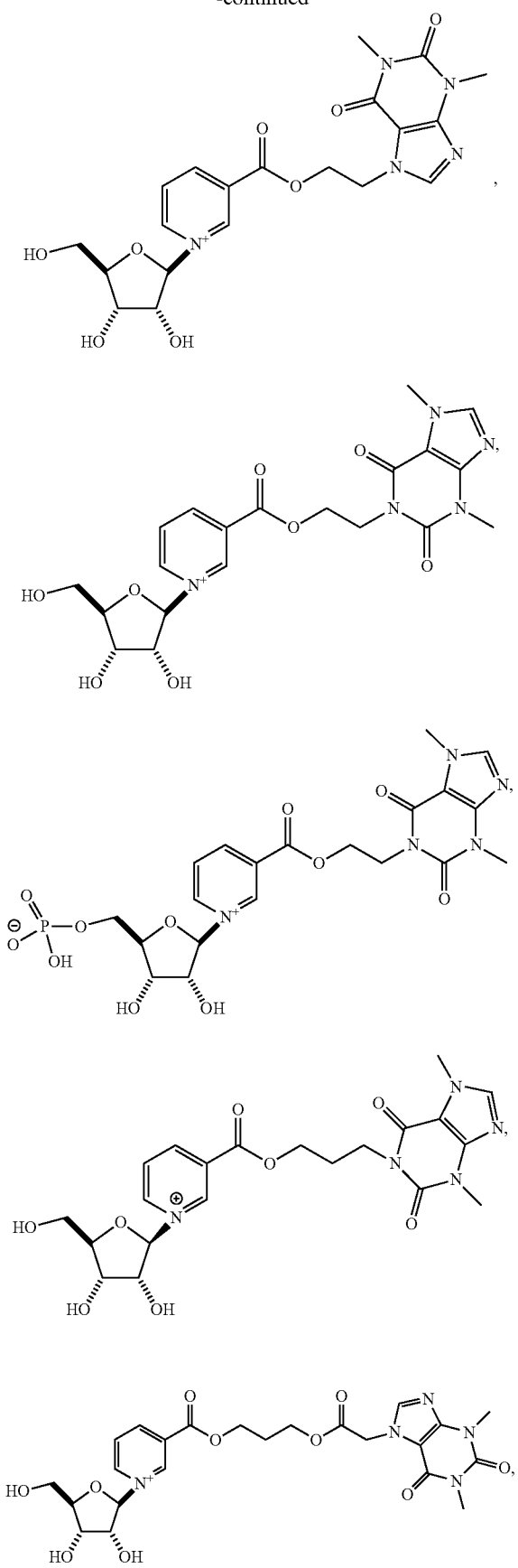

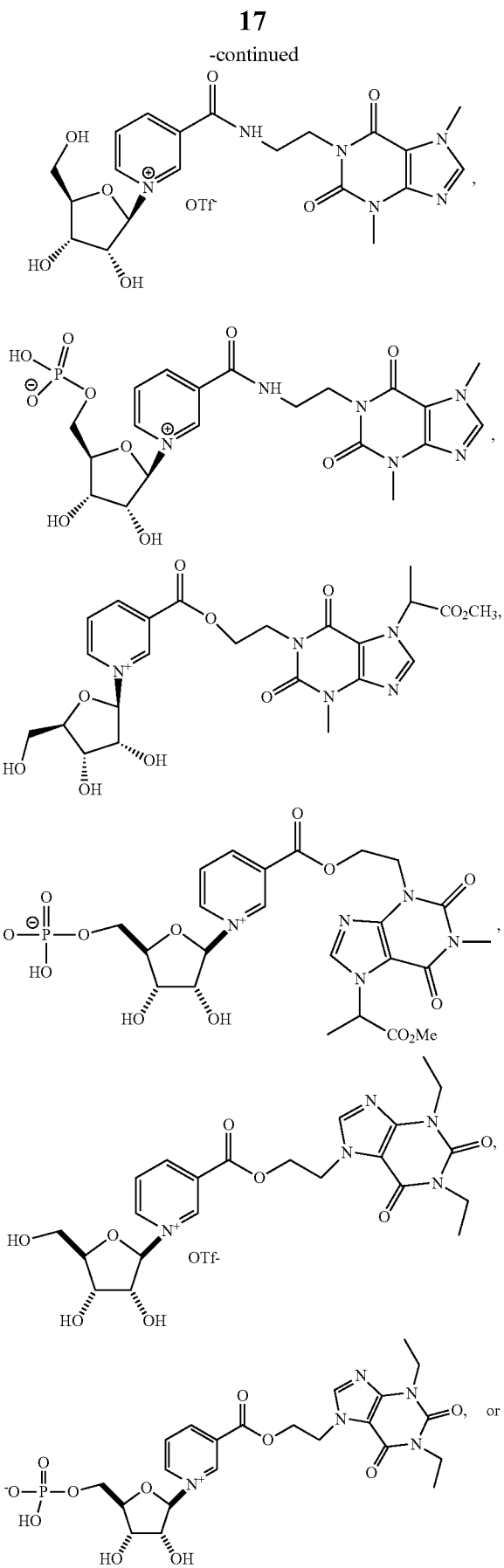

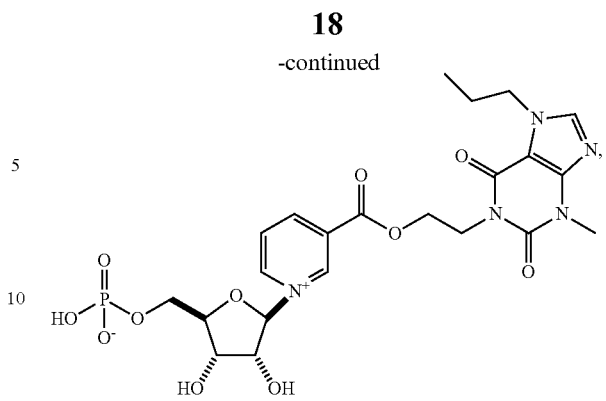

or a pharmaceutically acceptable salt thereof.

Compounds as disclosed herein may be synthesized according to general methods as known in the art, with various specific examples provided in the Examples herein. Modifications of the methods provided herein may be used to arrive at the full scope of the general Formula I.

Provided herein are pharmaceutically acceptable salts of a compound disclosed herein, wherein the salt comprises a cation selected from $H^+$, $Li^+$, $Na^+$, $K^+$, $Mg^{2+}$, and $Ca^{2+}$. In certain embodiments, the pharmaceutically acceptable salt comprises an anion selected from acetate, triflate, halide, trifluoroacetate, formate, $H_2PO_4^-$, $HPO_4^{2-}$, $OH^-$, $HSO_4^-$, $SO_4^{2-}$, $NO_3^-$, $HCO_3^-$, and $CO_3^{2-}$.

Disclosed herein are pharmaceutical compositions comprising a compound or pharmaceutically acceptable salt and one or more pharmaceutically acceptable excipients. In some embodiments, the pharmaceutically acceptable excipient is selected from an anti-adherent, a binder, a coating, a dye, a disintegrant, a flavoring agent, a glidant, a lubricant, a preservative, a sorbent, a sweetener, a dispersant, a diluent, a filler, a granulating agent, a coating agent, a wax, a suspending agent, a wetting agent, a vehicle, a liquid carrier, and combinations thereof. In certain embodiments, the composition is in a solid form selected from a tablet, a pill, a capsule, a caplet, a troche, granules, powders, a sachet, a dry powder inhalation form, a chewable, a pastille, and a lozenge. In some embodiments, the composition is in the form of a tablet. In some embodiments, one or more of the compounds and pharmaceutically acceptable salts are present in the composition in an amount from about 0.001% by weight to about 90% by weight.

Disclosed herein are methods treating inflammation in a subject, comprising administering a disclosed compound or pharmaceutically acceptable salt, or a pharmaceutical composition, to the subject. In certain embodiments, the inflammation is mediated by a phosphodiesterase. In other embodiments, the inflammation is related to asthma, chronic obstructive pulmonary disease (COPD), psoriasis, atopic dermatitis, inflammatory bowel disease (IBD), rheumatoid arthritis (RA), lupus, acute kidney injury (AKI), chronic kidney disease, or neuroinflammation. The phrase "related to" encompasses where the inflammation is the cause of the indication, or a symptom of the indication, or both. In various embodiments, disclosed herein are methods of treating asthma, chronic obstructive pulmonary disease (COPD), psoriasis, atopic dermatitis, inflammatory bowel disease (IBD), rheumatoid arthritis (RA), lupus, acute kidney injury (AKI), chronic kidney disease, or neuroinflammation.

Also disclosed herein are methods of treatment of acute kidney injury in a subject, said method comprising administering a compound or pharmaceutically acceptable salt of any one of the above clauses, or a pharmaceutical composition of any one of the above clauses, to the subject. Also disclosed herein are methods of treatment for increasing NAD+ in a subject, said method comprising administering a compound or pharmaceutically acceptable salt of any one of the above clauses, or a pharmaceutical composition of any one of the above clauses, to the subject.

In certain embodiments, the compound, the pharmaceutically acceptable salt, and/or the pharmaceutical composition is administered orally. In some embodiments, the oral administration occurs in an outpatient setting. In some embodiments, the subject performs the oral administration.

Compositions and Pharmaceutical Formulations

While it is possible for the active ingredients to be administered alone, it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

In some embodiments, the composition is in a solid form selected from a tablet, a pill, a capsule, a caplet, a troche, granules, powders, sachet, dry powder inhalation form, a chewable, a pastille, and a lozenge. In certain embodiments, the composition is in the form of a tablet. In other embodiments, the composition is in a form of a hard or soft gelatin capsule. Formulations of the present invention suitable for oral administration may be presented as discrete units such as capsules, cachets or tablets, each containing a predetermined amount of the active ingredient as a powder or granules. The active ingredient may also be administered as a bolus, electuary or paste.

In some embodiments, the pharmaceutically acceptable excipient is selected from an anti-adherent, binder, coating, dye, disintegrant, flavoring agent, glidant, lubricant, preservative, sorbent, sweetener, syrups, elixirs, dispersant, diluent, filler, granulating agent, coating agent, wax, suspending agent, wetting agent, thickener and vehicle and combinations thereof. In some embodiments, the excipient is a solid excipient.

In some embodiments, the pharmaceutically acceptable excipient is present in an amount of at least about 5% by weight, at least about 10% by weight, at least about 15% by weight, at least about 20% by weight, at least about 25% by weight, at least about 30% by weight, at least about 35% by weight, at least about 40% by weight, at least about 45% by weight, at least about 50% by weight, at least about 55% by weight, or at least about 60% by weight of the composition. In some embodiments, the pharmaceutically acceptable excipient is present in an amount of at least about 20% by weight, at least about 25% by weight, at least about 30% by weight, at least about 35% by weight, or at least about 40% by weight, preferably at least about 30% by weight of the composition. In other embodiments, the pharmaceutically acceptable excipient is present in an amount of at least about 50% by weight of the composition.

The compounds of this invention are formulated with conventional carriers and excipients, which can be selected in accord with ordinary practice. Tablets can contain excipients, glidants, fillers, binders and the like. All formulations will optionally contain excipients such as those set forth in the "Handbook of Pharmaceutical Excipients" (1986). Suitable excipients are also listed in the US Food and Drug Administration Inactive Ingredients Database. Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations can range from about 3 to about 11, but is ordinarily about 7 to about 10.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When intended for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques, including microencapsulation, to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active material(s) in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia; and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The amount of active ingredient that may be combined with the carrier material to produce a single dosage form will vary depending upon the subject treated and the particular mode of administration. For example, a time-release formulation intended for oral administration to humans may contain approximately 1 to approximately 1000 mg of active material compounded with an appropriate and convenient amount of carrier material which may vary from about 5% to about 95% of the total compositions (weight:weight). The pharmaceutical composition can be prepared to provide easily measurable amounts for administration.

Formulations suitable for intrapulmonary or nasal administration have a particle size for example in the range of about 0.1 to about 500 microns, such as about 0.5, about 1, about 30, or about 35 microns etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Methods of Treatment and Administration of Compounds

Provided herein are methods for using the disclosed compounds and pharmaceutical compositions thereof. The disclosed compounds and pharmaceutical compositions thereof can be useful for a variety of therapeutic applications including, for example, treating and/or reducing a wide variety of diseases and disorders including, for example, diseases or disorders related to inflammation. The methods comprise administering to a subject in need thereof a disclosed compound and/or pharmaceutical composition thereof.

Without wishing to be bound by theory, it is thought that phophodiesterases are involved in some inflammatory pathways. For example, it has been reported that phosphodiesterases (PDEs) degrade cyclic nucleotides including cyclic guanosine monophosphate (cGMP) and cyclic adenosine monophosphate (cAMP). cAMP and cGMP are critical second messengers in many signaling pathways. As such, targeting PDE4 may be an effective therapeutic strategy for inflammatory conditions including asthma, COPD, psoriasis, atopic dermatitis, IBD, Rheumatoid Arthritis, lupus, acute kidney injury (AKI), chronic kidney disease, and neuroinflammation. In various embodiments, provided herein are methods of treatment of acute kidney injury (AKI) by administration of a compound or composition as disclosed herein.

Also disclosed herein are methods of treatment of acute kidney injury in a subject, said method comprising administering a compound or pharmaceutically acceptable salt of any one of the above clauses, or a pharmaceutical composition of any one of the above clauses, to the subject. Also disclosed herein are methods of treatment for increasing NAD+ in a subject, said method comprising administering a compound or pharmaceutically acceptable salt of any one of the above clauses, or a pharmaceutical composition of any one of the above clauses, to the subject.

It should be understood that in addition to the ingredients particularly mentioned above, the formulations of this invention may include other agents conventional in the art having regard to the type of formulation in question.

EXAMPLES

Example 1

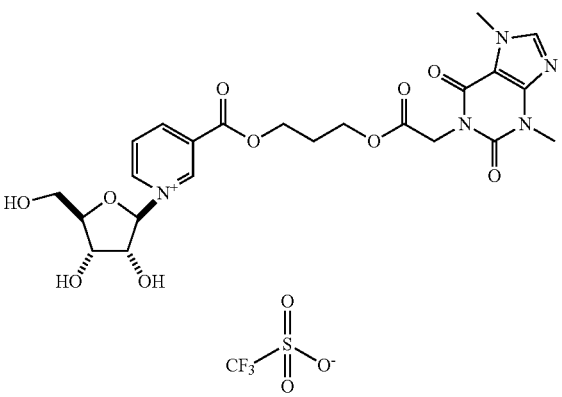

Compound 1

1-((2R,3R,4S,5R)-3,4-dihydroxy-5-(hydroxymethyl)
tetrahydrofuran-2-yl)-3-((3-(2-(3,7-dimethyl-2,6-
dioxo-2,3,6,7-tetrahydro-1H-purin-1-yl)acetoxy)
propoxy)carbonyl)pyridin-1-ium
trifluoromethanesulfonate

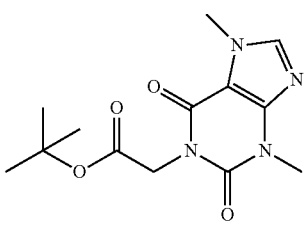 [SMILES: Cn1cnc2c1c(=O)n(CC(=O)OC(C)(C)C)c(=O)n2C]

tert-butyl 2-(3,7-dimethyl-2,6-dioxo-2,3,6,7-tetrahydro-1H-purin-1-yl)acetate. Theobromine (8.00 g, 44.0 mmol), tert-butyl bromoacetate (10.64 g, 54.5 mmol), potassium carbonate (12.16 g, 88.0 mmol), potassium iodide (7.30 g, 44.0 mmol), and benzyl trimethylammonium bromide (1.57 g, 4.4 mmol) were charged to a 100 mL, 1-necked, round bottomed flask. A magnetic stir bar was added, then anhydrous DMF (50 mL) was added, stirring was initiated, and the mixture was heated at 100° C. for 2 h. Additional tert-butyl bromoacetate (1.06 g, 5.43 mmol), was added, then the reaction was heated at 100° C. for 1 h. Heating was discontinued, and the reaction was allowed to stir at ambient temperature overnight. The mixture was concentrated in vacuo to a pasty solid. Dichloromethane (90 mL) was added, then the solution was filtered and the solid was washed with additional dichloromethane. The filtrate was extracted with water (2×60 mL), then the organic phase was dried over sodium sulfate. The solution was decanted from the solid and concentrated in vacuo to give a thick oil. The oil was triturated with heptanes two times, then placed under high vacuum to give a tan solid. The solid was treated with boiling water (60 mL) giving an oily layer and a solution. The solution was decanted from the oil. Upon cooling a white solid precipitated from the solution. After standing at 4 C for 18 h, the cold solution was filtered and washed with cold water. The solid was then dissolved in dichloromethane and the layers separated. The organic phase was dried over sodium sulfate, decanted, and concentrated in vacuo to give 5.80 gm of an off white solid, 45% yield.

LRMS (ESI)+ m/z: 295 [M+H]+. $^1$H NMR (CDCl$_3$) δ 7.54 (1H, s), 4.68 (2H, s), 3.99 (3H, s), 3.60 (3H, s), 1.51 (9H, s).

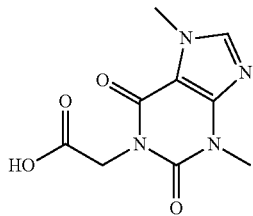 [SMILES: Cn1cnc2c1c(=O)n(CC(=O)O)c(=O)n2C]

2-(3,7-dimethyl-2,6-dioxo-2,3,6,7-tetrahydro-1H-purin-1-yl)acetic acid. A mixture of tert-butyl 2-(3,7-dimethyl-2,6-dioxo-2,3,6,7-tetrahydro-1H-purin-1-yl)acetate (3.00 g, 10.2 mmol) and 97% formic acid (10.98 g, 239 mmol) was placed into a 100 mL 1-necked round bottomed flask equipped with a magnetic stir bar. The reaction was heated at 55° C. for 18 h, then it was cooled and concentrated in vacuo. The resulting white solid was washed with dichloromethane, filtered, and dried in vacuo to give 2.35 g of the product, 97% yield.

LRMS (ESI)+ m/z: 239 [M+H]+.

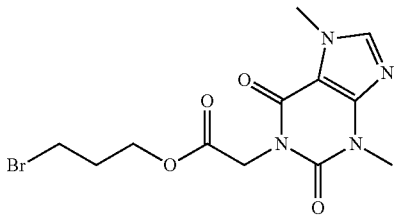 [SMILES: Cn1cnc2c1c(=O)n(CC(=O)OCCCBr)c(=O)n2C]

3-bromopropyl 2-(3,7-dimethyl-2,6-dioxo-2,3,6,7-tetrahydro-1H-purin-1-yl)acetate. 2-(3,7-dimethyl-2,6-dioxo-2,3,6,7-tetrahydro-1H-purin-1-yl)acetic acid (2.35 g, 9.84 mmol) was placed into a 100 mL 1-necked round bottomed flask equipped with a 24/40 septum and a magnetic stir bar and placed under argon. Acetonitrile (anhydrous, 12 mL) was added via syringe and thionyl chloride (2.34 g, 19.7 mmol) was added dropwise over 5 min. The reaction was kept under an argon balloon and heated with a 40° C. oil bath for 1 hour. The solvent was evaporated in vacuo, then dry acetonitrile (10 mL) was added and evaporated again to remove the traces of acid left. Another portion of dry acetonitrile (20 mL) was added. 3-bromo-1-propanol (1.43 g, 10.3 mmol) and triethylamine (1.09 g, 10.8 mmol) were added in succession, dropwise, at room temperature via syringe. After stirring for 20 minutes the reaction was heated with a 50° C. oil bath for 2 hours. The reaction was concentrated in vacuo and the residue dissolved in dichloromethane (20 mL). The organic phase was washed with saturated sodium bicarbonate solution (30 mL) and dried over sodium sulfate. The solution was decanted, then concentrated in vacuo to give a solid that was dissolved in a minimum of ethyl acetate. Addition of hexanes then gave 2.21 g of a tan solid, 63% yield.

LRMS (ESI)+ m/z: 360 [M+H]+.

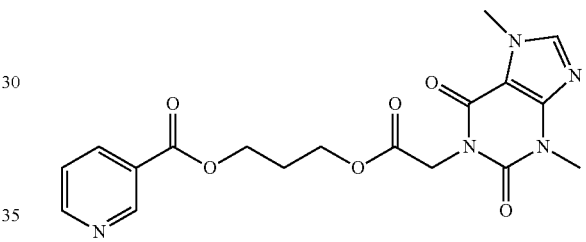

3-(2-(3,7-dimethyl-2,6-dioxo-2,3,6,7-tetrahydro-1H-purin-1-yl)acetoxy)propyl nicotinate. 3-bromopropyl 2-(3,7-dimethyl-2,6-dioxo-2,3,6,7-tetrahydro-1H-purin-1-yl)acetate (2.43 g, 6.77 mmol), sodium nicotinate (1.00 g, 6.91 mmol), benzyltrimethylammonium bromide (0.48 g, 1.35 mmol), and potassium iodide (0.224 g, 1.35 mmol) were placed into a 100 mL one-necked round bottomed flask with a magnetic stir bar and a 14/40 rubber septum under an argon balloon. DMF (anhydrous, 15 mL) was added and the reaction was stirred and heated with a 95° C. oil bath for 2 hours. The reaction was concentrated in vacuo and co-evaporated with acetonitrile (2×20 mL). The resulting foam was titrated with MTBE (3×20 mL), placed under high vacuum and then dissolved in DCM. The resulting solution was filtered and the filtrate concentrated in vacuo. The residue was redissolved in DCM, washed with saturated sodium bicarbonate (2×20 mL), dried over sodium sulfate, decanted and concentrated in vacuo to give 2.53 gm of crude product. This was purified via silica gel chromatography (20 g column) and eluting with a gradient of 100% dichloromethane to 5% methanol/dichloromethane. The product came off with 1% MeOH/DCM, the appropriate fractions were collected and concentrated to give 1.93 g (71%) of the product.

LRMS (ESI)+ m/z: 402 [M+H]+.

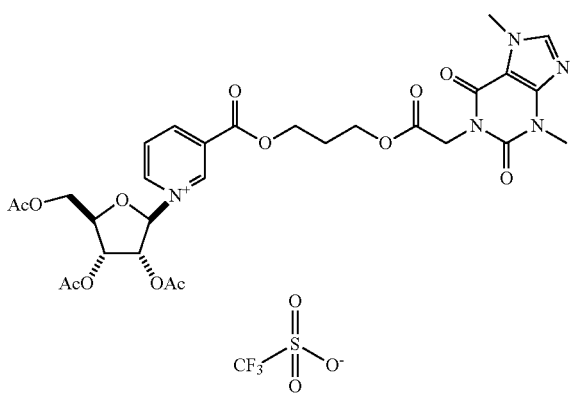

1-((2R,3R,4R,5R)-3,4-diacetoxy-5-(acetoxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate.

3-(2-(3,7-dimethyl-2,6-dioxo-2,3,6,7-tetrahydro-1H-purin-1-yl)acetoxy)propyl nicotinate (1.80 g, 4.48 mmol) and β-D-ribofuranose-1,2,3,5-tetraacetate (1.43 g, 4.48 mmol) were placed into a 100 mL, 1-necked 24/40 round bottomed flask equipped with a magnetic stir bar and capped with a 24/40 rubber septum. The headspace was evacuated and placed under argon, then dichloromethane (18 mL) was added via syringe. The mixture was stirred at room temperature as trimethylsilyl trifluoromethanesulfonate (2.11 g, 9.50 mmol) was added via syringe over 5 minutes. The reaction was stirred for 1 hour, then the solution was extracted with saturated aqueous sodium bicarbonate (1×20 mL). The layers were separated and the organic phase was dried over sodium sulfate, decanted, and concentrated in vacuo to give a yellow foam, 3.62 g, 100% yield. LRMS (ESI)$^+$ m/z: 660 [M]$^+$.

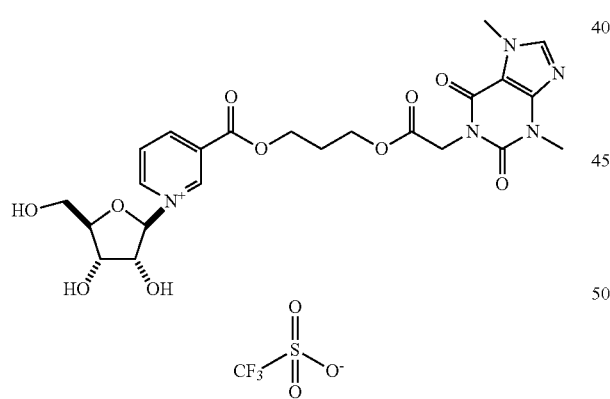

1-((2R,3R,4S,5R)-3,4-dihydroxy-5-(hydroxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate Acetyl chloride (2.11 g, 26.9 mmol) was added dropwise to dry, cold anhydrous methanol (20 mL) with stirring, and this cold, acidic solution was added to 1-((2R,3R,4R,5R)-3,4-diacetoxy-5-(acetoxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate (3.62 g, 4.48 mmol) all while keeping the reagents cold and under argon. After stirring overnight at 4° C., the product was precipitated using MTBE. This process of dissolving the crude product in methanol and precipitation with MTBE was repeated until a foam or glass, 2.30 g, was obtained. Purification via silica gel chromatography, using a gradient of 100% dichloromethane to a 30% methanol/70% dichloromethane solvent system gave the desired product, 0.665 g, 21.7% yield LRMS (ESI)$^+$ m/z: 534.2 [M]$^+$ H NMR (D$_2$O) δ 9.70 (s, 1H), 9.30 (d, 1H), 9.07 (d, 1H), 8.29 (m, 1H), 7.80 (s, 1H), 6.23 (d, 1H), 5.19 (s, 2H), 4.47 (m, 2H), 4.39 (m, 4H), 4.33 (t, 1H), 4.01 (d of d, 1H), 3.90 (d of d, 1H), 3.51 (s, 3H), 3.21 (s, 3H), 2.16 (m, 2H).

Example 2

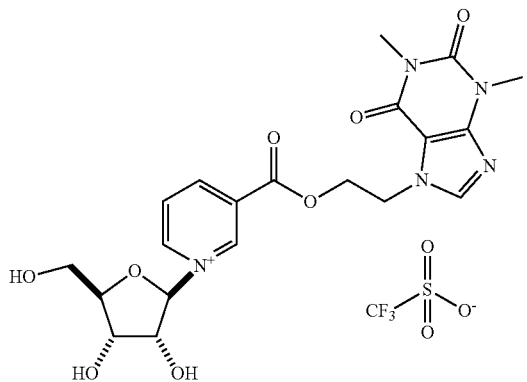 [SMILES: Cn1c(=O)c2c(ncn2CCOC(=O)c2ccc[n+]([C@@H]3O[C@H](CO)[C@@H](O)[C@H]3O)c2)n(C)c1=O ; O=S(=O)([O-])C(F)(F)F]

Compound 2

1-((2R,3R,4S,5R)-3,4-dihydroxy-5-(hydroxymethyl)tetrahydrofuran-2-yl)-3-((2-(1,3-dimethyl-2,6-dioxo-1,2,3,6-tetrahydro-7H-purin-7-yl)ethoxy)carbonyl)pyridin-1-ium trifluoromethanesulfonate

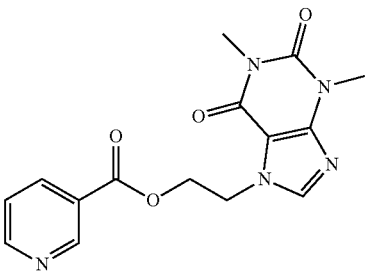 [SMILES: Cn1c(=O)c2c(ncn2CCOC(=O)c2cccnc2)n(C)c1=O]

2-(1,3-dimethyl-2,6-dioxo-1,2,3,6-tetrahydro-7H-purin-7-yl)ethyl nicotinate. A 100 mL one-necked round bottomed flask equipped with a magnetic stir bar and a rubber septum was charged with 7-(2-hydroxyethyl)-1,3-dimethyl-3,7-dihydro-1H-purine-2,6-dione (5.00 g, 22.3 mmol), nicotinic acid (2.75 g, 22.3 mmol), and 1-(3-Dimethylaminopropyl)-3-ethylcarbodiimide hydrochloride (4.28 g, 22.3 mmol), then the headspace was purged with argon. Dichloromethane (40 mL) was added and stirring was initiated to give a suspension. Next, 4-N,N-dimethylaminopyridine (0.55 g, 4.50 mmol), was added and the reaction was stirred at ambient temperature for 2 hours. Saturated sodium bicarbonate (30 mL) was added, then the mixture was transferred to a separatory funnel. The organic phase was separated, dried over sodium sulfate, decanted and concentrated in vacuo to give 6.70 g of crude product. This was purified utilizing silica gel (65 g) and elution with a gradient of 100% dichloromethane to 97:3 (v:v) dichloromethane:methanol, giving 5.50 g of a white solid, 74.9% yield.

LRMS (ESI)+ m/z: 330 [M+H]+.

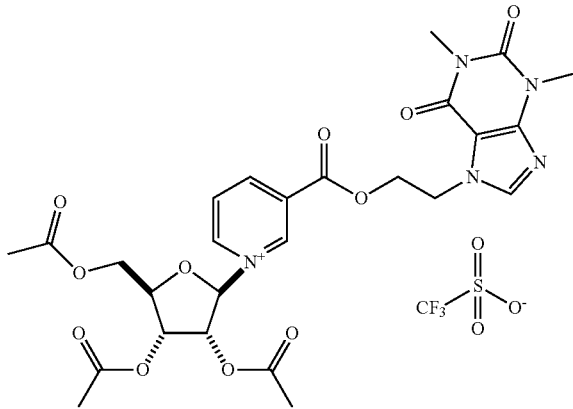 [SMILES: CC(=O)OC[C@H]1O[C@@H]([n+]2cccc(C(=O)OCCn3cnc4c3c(=O)n(C)c(=O)n4C)c2)[C@H](OC(C)=O)[C@@H]1OC(C)=O ; O=S(=O)([O-])C(F)(F)F]

1-((2R,3R,4R,5R)-3,4-diacetoxy-5-(acetoxymethyl)tetrahydrofuran-2-yl)-3-((2-(1,3-dimethyl-2,6-dioxo-1,2,3,6-tetrahydro-7H-purin-7-yl)ethoxy)carbonyl)pyridin-1-ium trifluoromethanesulfonate 2-(1,3-dimethyl-2,6-dioxo-1,2,3,6-tetrahydro-7H-purin-7-yl)ethyl nicotinate (5.50 g, 16.70 mmoles) and β-D-ribofuranose-1,2,3,5-tetraacetate (5.31 g, 16.70 mmoles) were combined in a 500 mL 1 necked round bottomed flask with a magnetic stir bar and a 24/40 septum and placed under argon. Dry dioxane (50 mL) was added via syringe and trimethylsilyl trifluoromethyl sulfonate (7.42 g, 33.4 mmoles) was added dropwise over 10 minutes. The reaction was heated in a 40° C. oil bath for 15 hours then allowed to cool to room temperature. MTBE was added to precipitate the product. The solvents were decanted from the solid, which was dissolved in ACN (minimum) and re-precipitated by the addition of MTBE. This process was repeated using ACN and MTBE after decanting the solvent from the solid. The resulting solid was placed under high vacuum, giving 19.3 g (157%, still containing some solvent).

LRMS (ESI)+ m/z: 588 [M]+.

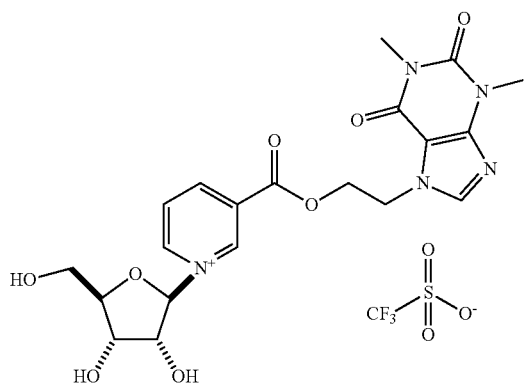 [SMILES: Cn1c(=O)c2c(ncn2CCOC(=O)c2ccc[n+]([C@@H]3O[C@H](CO)[C@@H](O)[C@H]3O)c2)n(C)c1=O ; O=S(=O)([O-])C(F)(F)F]

1-((2R,3R,4S,5R)-3,4-dihydroxy-5-(hydroxymethyl)tetrahydrofuran-2-yl)-3-((2-(1,3-dimethyl-2,6-dioxo-1,2,3,6-tetrahydro-7H-purin-7-yl)ethoxy)carbonyl)pyridin-1-ium trifluoromethanesulfonate Prepared using a procedure similar to that used for 1-((2R,3R,4S,5R)-3,4-dihydroxy-5-(hydroxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate. The yield was 8.66 g, 85%.

LRMS (ESI)+ m/z: 462 [M]+. 1HNMR (D2O) δ 9.62 (s, 1H), 9.25 (d, 1H), 8.98 (d, 1H), 8.25 (d of d, 1H), 8.07 (s, 1H), 6.20 (d, 1H), 4.86 (m, 1H), 4.75 (m, 1H), 4.42 (t, 1H), 4.28 (t, 1H), 3.90 (d of d, 1H), 3.81 (d of d, 1H) 3.46 (s, 3H), 3.14 (s, 3H).

Example 2P

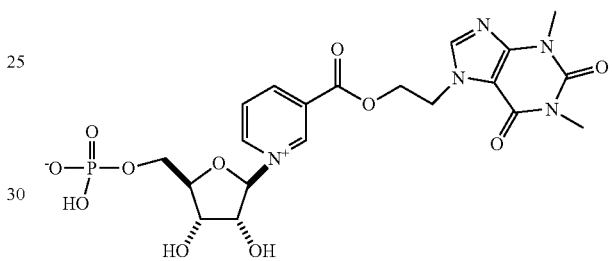

Compound 2P ((2R,3S,4R,5R)-5-(3-((2-(1,3-dimethyl-2,6-dioxo-1,2,3,6-tetrahydro-7H-purin-7-yl)ethoxy)carbonyl)pyridin-1-ium-1-yl)-3,4-dihydroxytetrahydrofuran-2-yl)methyl hydrogen phosphate Compound 2 (5.00 g, 8.18 mmoles) was added to a 200 mL one necked round bottomed flask along with a magnetic stir bar and rubber septum in an ice water bath. The flask was evacuated and placed under argon. Dry TMP (25 mL) was added via syringe and stirred. The mixture became a semi solid mass. Phosphorous oxychloride was added dropwise via syringe but the mass did not break up. A spatula was used to carefully break up the solid until it could be stirred. After 6.5 hours, 8% of the starting material remained. At 7 hours after the reaction start, water (4.42 g, 245 mmoles) was added slowly dropwise to the cold reaction over 10 minutes. The reaction was stirred for 5 minutes then placed into a −25° C. freezer overnight. The reaction was placed into an ice water bath and was a gelatinous mass. IPA (25 mL) was added and the gel broken up cautiously using a spatula. Triethylamine (4.98 g, 49.2 mmoles) was added to IPA (15 mL). This solution was added cautiously to the cold reaction mixture until the pH was measured at 3.0. Once this pH was achieved the reaction was stirred for 30 minutes in the ice water bath, then filtered and the isolated solid washed with IPA then MTBE. The light yellow solid was dried in vacuo giving 4.03 g of crude product. A portion of this was purified using a 40 g C-18 column with a gradient of 5-30% methanol in water as eluent. LRMS (ESI)+ m/z: 542.2

Example 3

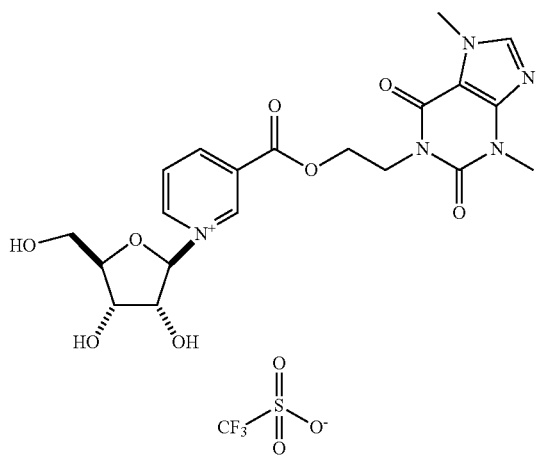

Compound 3

1-((2R,3R,4S,5R)-3,4-dihydroxy-5-(hydroxymethyl)tetrahydrofuran-2-yl)-3-((2-(3,7-dimethyl-2,6-dioxo-2,3,6,7-tetrahydro-1H-purin-1-yl)ethoxy)carbonyl)pyridin-1-ium trifluoromethanesulfonate

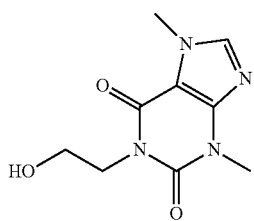 [SMILES: Cn1cnc2c1c(=O)n(CCO)c(=O)n2C]

1-(2-hydroxyethyl)-3,7-dimethyl-3,7-dihydro-1H-purine-2,6-dione

A 500 mL 1-necked round bottomed flask was charged with theobromine (10.0 g, 55.5 mmol) and potassium carbonate (8.50 g, 61.5 mmol, crushed). A magnetic stir bar was added, then the headspace was purged with argon. Next, DMF (100 mL) was added via syringe, and stirring was initiated. The flask was heated with a 140° C. oil bath for 40 min, and the mixture became thick during this time. During this time, another aliquot of DMF (40 mL) was added to ease the stirring. After the 40 minute heating period, 2-iodoethanol (9.53 g, 55.5 mmol) was added dropwise over 10 minute period. 50 minutes after the addition of the first aliquot, a second aliquot of 2-iodoethanol (1.47 g, 8.54 mmol) was added over 5 min. After stirring for an additional 30 min, a third aliquot of 2-iodoethanol (2.47 g, 14.4 mmol) was added. The reaction was stirred for another 30 min, then a fourth aliquot of 2-iodoethanol (1.88 g, 10.9 mmol) was added. The mixture was stirred at 140° C. for 18 h, then cooled to ambient temperature. The reaction was filtered, and concentrated in vacuo, then the residue was left under high vacuum overnight. This gave an off white solid which was swirled with acetone (50 mL). The resulting solid was filtered, washed with acetone, then placed under high vacuum. The resulting solid (29.59 g) was dissolved in boiling EtOH (500 mL) then the solution was allowed to cool. The resulting solid was filtered, washed with additional ethanol, and dried under high vacuum to give 14.63 g of product, 110% yield.

LRMS (ESI)$^+$ m/z: 225 [M+H]$^+$. $^1$H NMR (D$_2$O) δ 7.85 (1H, s), 4.1 (2H, t), 3.9 (3H, s), 3.7 (2H, t), 3.5 (3H, s).

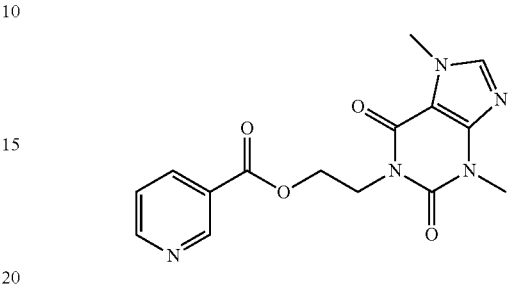

2-(3,7-dimethyl-2,6-dioxo-2,3,6,7-tetrahydro-1H-purin-1-yl)ethyl nicotinate 2-(3,7-dimethyl-2,6-dioxo-2,3,6,7-tetrahydro-1H-purin-1-yl)ethyl nicotinate was prepared using a similar method to that which was used to prepare 2-(1,3-dimethyl-2,6-dioxo-1,2,3,6-tetrahydro-7H-purin-7-yl)ethyl nicotinate. Utilizing 12.6 g (52.9 mmoles) of 1-(2-hydroxyethyl)-3,7-dimethyl-3,7-dihydro-1H-purine-2,6-dione, 6.59 g (53.5 mmoles) of nicotinic acid, 11.35 g (59.20 mmoles) of 1-(3-Dimethylaminopropyl)-3-ethylcarbodiimide hydrochloride and 1.31 g of DMAP (10.7 mmoles) in DCM (75 mL) a yield of 82% of the 2-(3,7-dimethyl-2,6-dioxo-2,3,6,7-tetrahydro-1H-purin-1-yl)ethyl nicotinate (13.58 g) was obtained.

LRMS (ESI)$^+$ m/z: 330.

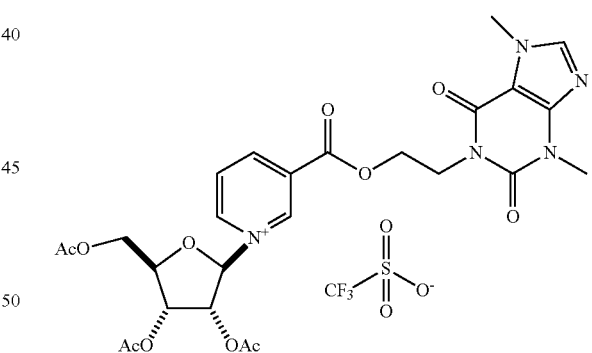

1-((2R,3R,4R,5R)-3,4-diacetoxy-5-(acetoxymethyl)tetrahydrofuran-2-yl)-3-((2-(3,7-dimethyl-2,6-dioxo-2,3,6,7-tetrahydro-1H-purin-1-yl)ethoxy)carbonyl)pyridin-1-ium trifluoromethanesulfonate Prepared using a similar procedure to 1-((2R,3R,4R,5R)-3,4-diacetoxy-5-(acetoxymethyl)tetrahydrofuran-2-yl)-3-((2-(1,3-dimethyl-2,6-dioxo-1,2,3,6-tetrahydro-7H-purin-7-yl)ethoxy)carbonyl)pyridin-1-ium trifluoromethanesulfonate except that the reaction only required 1 hour at 40° C. to complete.

2-(3,7-dimethyl-2,6-dioxo-2,3,6,7-tetrahydro-1H-purin-1-yl)ethyl nicotinate (13.00 g, 39.5 mmoles) and β-D- ribofuranose-1,2,3,5-tetraacetate (12.94 g, 40.7 mmoles) were combined and dry dioxane (100 mL) was added. After stirring was initiated, the trimethylsilyl trifluoromethanesulfonate (9.66 g, 43.45 mmoles) was added dropwise over 10 minutes. An alternate workup was employed. The reaction was removed from the warm oil bath and allowed to cool to room temperature. DCM (50 mL) was added and then saturated sodium bicarbonate solution (50 mL). This biphasic solution was stirred for 10 minutes then separated and the organic solution was dried over sodium sulfate. The organic solution was concentrated in vacuo to give a yellow foam, 29.17 g, 97.2%.

LRMS (ESI)+ m/z: 588

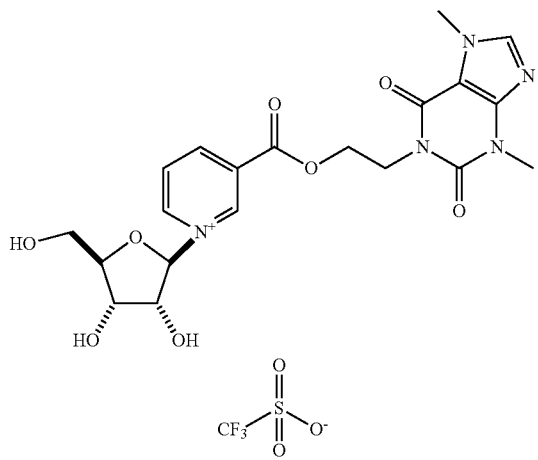

1-((2R,3R,4S,5R)-3,4-dihydroxy-5-(hydroxymethyl) tetrahydrofuran-2-yl)-3-((2-(3,7-dimethyl-2,6-dioxo-2,3,6,7-tetrahydro-1H-purin-1-yl)ethoxy)carbonyl) pyridin-1-ium trifluoromethanesulfonate Prepared using a similar procedure as was used for the preparation of 1-((2R,3R,4S,5R)-3,4-dihydroxy-5-(hydroxymethyl)tetrahydrofuran-2-yl)-3-((3-(2-(3,7-dimethyl-2,6-dioxo-2,3,6,7-tetrahydro-1H-purin-1-yl)acetoxy) propoxy)carbonyl)pyridin-1-ium trifluoromethanesulfonate.

1-((2R,3R,4R,5R)-3,4-diacetoxy-5-(acetoxymethyl)tetrahydrofuran-2-yl)-3-((2-(3,7-dimethyl-2,6-dioxo-2,3,6,7-tetrahydro-1H-purin-1-yl)ethoxy)carbonyl)pyridin-1-ium trifluoromethanesulfonate (29.17 g, 39.5 mmoles) was deprotected by treatment with a cold methanolic HCl solution generated from acetyl chloride (18.63 g, 237 mmoles) in cold methanol (120 mL). Precipitation using MTBE (approximately 400 mL) and decantation of the solvents was followed by re-dissolving to resulting glass in a minimum of methanol and reprecipitation using MTBE a total of four more times gave an off white solid (15.20 g, 62.9%) after being placed under high vacuum for 18 hours.

LRMS (ESI)+ m/z: 462

Example 4

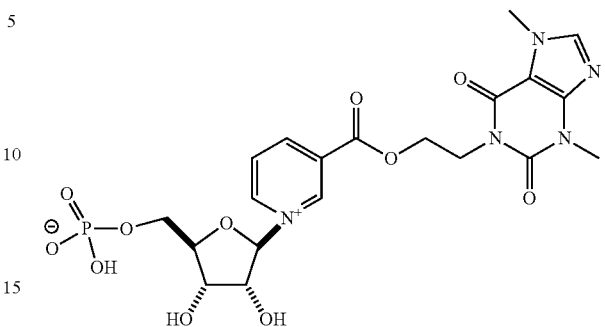

Compound 4

((2R,3S,4R,5R)-5-(3-((2-(3,7-dimethyl-2,6-dioxo-2,3,6,7-tetrahydro-1H-purin-1-yl)ethoxy)carbonyl) pyridin-1-ium-1-yl)-3,4-dihydroxytetrahydrofuran-2-yl)methyl hydrogen phosphate 1-((2R,3R,4S,5R)-3,4-dihydroxy-5-(hydroxymethyl)tetrahydrofuran-2-yl)-3-((2-(3,7-dimethyl-2,6-dioxo-2,3,6,7-tetrahydro-1H-purin-1-yl)ethoxy)carbonyl)pyridin-1-ium trifluoromethanesulfonate (3.00 g, 4.91 mmoles) was placed into a 100 mL, 1 necked 24/40 round bottomed flask with a magnetic stir bar and a 24/40 septum and placed under Argon in an ice/water bath. TMP (20 mL, over sieves and under Argon) was added to the flask via syringe. The reaction is kept in the ice/water bath during the entire reaction. This gave a heterogeneous solution upon stirring. After 10 minutes, 2 was added dropwise via syringe over a 5 minute period. After 1 hour, 3 was added dropwise via syringe over 2 minutes. After 3 hours, HPLC showed the reaction to be nearly complete. After 3 hours and 10 minutes, 4 was added dropwise over 5 minutes, the reaction went from heterogeneous to homogeneous at this point. 5 was added to IPA (200 mL) in a 500 mL Erlenmeyer flask and this solution was placed into a cold bath and sealed with parafilm under an Argon blanket. The reaction mixture was added dropwise to the IPA solution over 8 minutes and then stirred for 30 minutes. pH was measured as 2 (pH 0-14 paper). The resulting suspension was stirred cold for 30 minutes then filtered and washed with cold IPA then placed under high vacuum. This gave 3.39 gm of crude product (131% yield). 2.50 gms of crude product was purified on an Interchim chromatography system using a solvent system of 95% ACN:$H_2O$ (100 mM formic acid) to 95:5 $H_2O$:ACN (100 mM formic acid). The appropriate fractions were combined and concentrated at 20-23° C. under high vacuum to give 1.62 g of product.

$^1$H NMR ($D_2O$) δ 9.41 (s, 1H), 9.32 (d, 1H), 8.99 (d, 1H), 8.28 (m, 1H), 7.85 (s, 1H), 6.17 (d, 1H), 4.72 (m, 1H), 4.62 (m, 1H), 4.50 (m, 1H), 4.37 (m, 3H), 4.06 (m, 2H), 3.83 (s, 3H), 3.42 (s, 3H); 31 P ($D_2O$) δ −0.1; LRMS (ESI)+ m/z: 462

Example 5

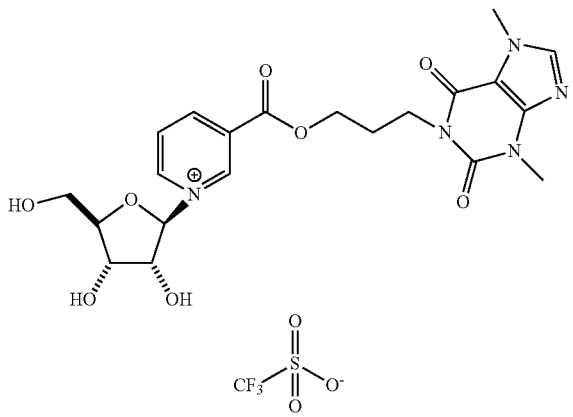

Compound 5

1-((2R,3R,4S,5R)-3,4-dihydroxy-5-(hydroxymethyl)
tetrahydrofuran-2-yl)-3-((3-(3,7-dimethyl-2,6-dioxo-
2,3,6,7-tetrahydro-1H-purin-1-yl)propoxy)carbonyl)
pyridin-1-ium trifluoromethanesulfonate

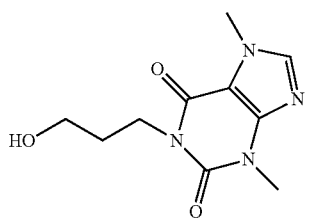 [SMILES: Cn1cnc2c1c(=O)n(CCCO)c(=O)n2C]

1-(3-hydroxypropyl)-3,7-dimethyl-3,7-dihydro-1H-
purine-2,6-dione

Theobromine (6.00 g, 33.3 mmoles), potassium iodide (11.06 g, 66.7 mmoles) and crushed potassium carbonate (5.08 g, 36.8 mmoles) were placed into a 100 mL 24/40 one necked round bottomed flask along with a magnetic stir bar and 24.40 rubber septum. The flask was evacuated and placed under argon. Dry DMF (70 mL) was added via syringe and the reaction heated in a 140° C. oil bath. After 15 minutes, the first aliquot of 3-chloro-1-propanol (3.14 g, 33.3 mmoles) was added dropwise over 5 minutes with a syringe. After 2 hours, another aliquot of 3-chloro-1-propanol (0.88 g, 9.32 mmoles) was added dropwise. The reaction was kept at this temperature for another 45 minutes and then the temperature was reduced to for 18 hours. The reaction was hot filtered and the solvent removed under high vacuum. Ethanol (100 mL) was added to the pasty white solid and this solution was heated in an 80° C. oil bath. This solution was hot filtered and the ethanol removed in vacuo, giving a gummy semi-solid. This was titrated with MTBE three times and the resulting solid was placed under high vacuum to remove the trace of MTBE left. The solid was heated with ethanol (70 mL), giving a solid and a liquid phase, which was decanted from the solid. The solid was washed with 5% methanol/DCM (50 mL) and the liquid was combined with the ethanol solution and concentrated in vacuo. The resulting solid (8.05 g) was treated with acetone (50 mL), stirred for 30 minutes, filtered and the solid was isolated and dried in vacuo, giving 5.95 g of product.

LRMS (ESI)+ m/z: 239

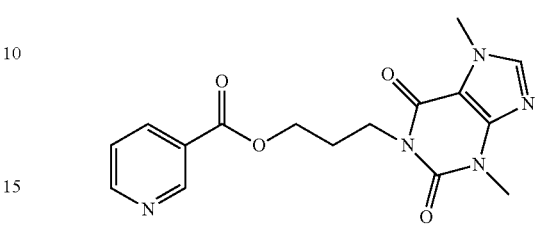

3-(3,7-dimethyl-2,6-dioxo-2,3,6,7-tetrahydro-1H-
purin-1-yl)propyl nicotinate was prepared in a manner similar to the preparation of 2-(1,3-dimethyl-2,
6-dioxo-1,2,3,6-tetrahydro-7H-purin-7-yl)ethyl
nicotinate 1-(3-hydroxypropyl)-3,7-dimethyl-3,7-dihydro-1H-purine-2,6-di one (5.95 g, 25.0 mmoles), nicotinic acid (3.07 g, 25.0 mmoles), 1-(3-Dimethylaminopropyl)-3-ethylcarbodiimide hydrochloride (5.03 g, 26.2 mmoles) and dimethylaminopyridine (0.614 g, 5.02 mmoles) were combined in a 100 mL 24/40 one necked round bottomed flask with a magnetic stir bar and 24/40 rubber septum and placed under argon. DCM (40 mL) was added and the reaction was stirred for 1.5 hours at room temperature. Workup with saturated sodium bicarbonate, drying with sodium sulfate, decantation and concentration in vacuo gave 7.47 g of product, 87.2% yield.

LRMS (ESI)+ m/z: 344.

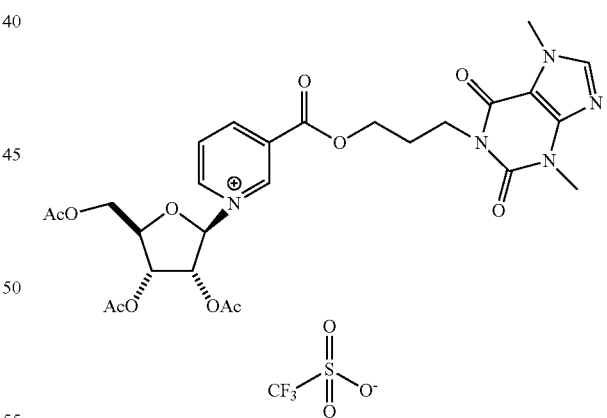

1-((2R,3R,4R,5R)-3,4-diacetoxy-5-(acetoxymethyl)
tetrahydrofuran-2-yl)-3-((3-(3,7-dimethyl-2,6-dioxo-
2,3,6,7-tetrahydro-1H-purin-1-yl)propoxy)carbonyl)
pyridin-1-ium trifluoromethanesulfonate This was prepared using a similar method to that which was used to prepare 1-((2R,3R,4R,5R)-3,4-diacetoxy-5-(acetoxymethyl)tetrahydrofuran-2-yl)-3-((2-(3,7-dimethyl-2,6-dioxo-2,3,6,7-tetrahydro-1H-purin-1-yl)ethoxy)carbonyl)pyridin-1-ium trifluoromethanesulfonate.

3-(3,7-dimethyl-2,6-dioxo-2,3,6,7-tetrahydro-1H-purin-1-yl)propyl nicotinate (7.37 g, 21.5 mmoles) and β-D-ribofuranose-1,2,3,5-tetraacetate (6.83 g, 21.5 mmoles) were combined under argon and dry dioxane (40 mL) was added. Trimethylsilyl trifluoromethanesulfonate (9.76 g, 43.91 mmoles) was added dropwise via syringe and the reaction was heated at 42° C. for 18 hours. This gave a biphasic reaction mixture which was added to well stirred MTBE (150 mL). The resulting gummy solid was dissolved in a minimum of ACN and precipitated by adding the solution to MTBE with stirring, this was repeated three times, the resulting gum was placed under a high vacuum, giving a yellow foam, 16.62 g, 103% yield.

LRMS (ESI)⁺ m/z: 602.

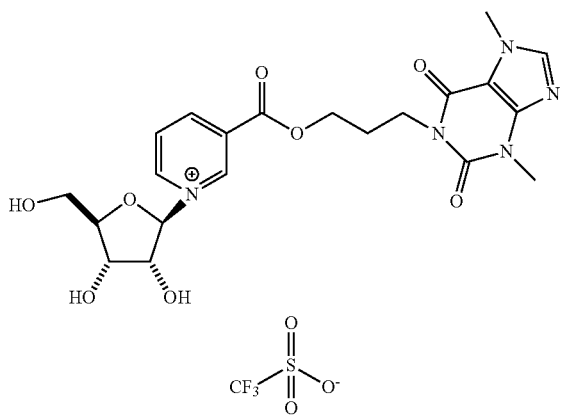

1-((2R,3R,4S,5R)-3,4-dihydroxy-5-(hydroxymethyl)tetrahydrofuran-2-yl)-3-((3-(3,7-dimethyl-2,6-dioxo-2,3,6,7-tetrahydro-1H-purin-1-yl)propoxy)carbonyl)pyridin-1-ium trifluoromethanesulfonate Prepared using a similar procedure as was used for the preparation of 1-((2R,3R,4S,5R)-3,4-dihydroxy-5-(hydroxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate.

1-((2R,3R,4R,5R)-3,4-diacetoxy-5-(acetoxymethyl)tetrahydrofuran-2-yl)-3-((3-(3,7-dimethyl-2,6-dioxo-2,3,6,7-tetrahydro-1H-purin-1-yl)propoxy)carbonyl)pyridin-1-ium trifluoromethanesulfonate (16.62 g, 22.1 mmoles) gave 10.83 g of crude product (78.4% yield).

A sample of this product (2.50 g) was purified using silica gel (25 g) and DCM to 20% methanol/DCM as eluent to give 1.15 g of purified product.

LRMS (ESI)⁺ m/z: 476; 1 H NMR (D₂O) δ 9.70 (1H, s), 9.27 (1H, d), 9.03 (1H, s), 8.24 (1H, d of d), 7.82 (1H, s), 6.20 (1H, d), 4.50-4.44 (4H, m), 4.32 (1H, t), 4.13 (1H, t), 4.00 (1H, d of d), 3.98 (1H, d of d), 3.82 (3H, s), 2.98 (3H, s), 2.16 (2H, t).

Example 5P

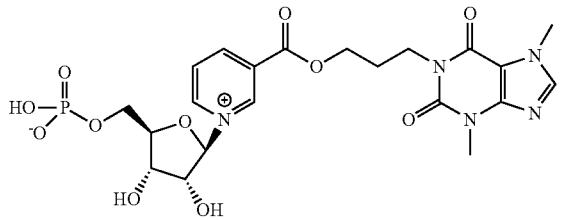

Compound 5P ((2R,3S,4R,5R)-5-(3-((3-(3,7-dimethyl-2,3,6,7-tetrahydro-1H-purin-1-yl)propoxy)carbonyl)pyridin-1-ium-1-yl)-3,4-dihydroxytetrahydrofuran-2-yl)methyl hydrogen phosphate This was prepared using a modification of the procedure for the synthesis of Compound 9P.

Compound 5 (2.5 g, 4.00 mmoles) was reacted with phosphorous oxychloride (1.23 g, 8.00 mmoles) in dry trimethyl phosphate (15 mL) at 0° C. for 7 hours. The reaction was quenched with water (3.36 g, 24.0 mmoles) and neutralized with triethylamine (2.43 g, 24.0 mmoles). This reaction mixture was added dropwise to isopropanol (400 mL) and the resulting precipitate was isolated by filtration, washed with isopropanol and then MTBE. Upon drying this gave 2.00 g of crude product, a portion of which was purified by chromatography on a 40 g C-18 reverse phase column using a gradient of 5-30% methanol water solvent. This gave 330 mg of purified product.

LRMS (ESI)⁺ m/z: 556.1; ¹H NMR (D₂O) δ 9.44 (s, 1H), 9.33 (d, 1H), 9.01 (d, 1H), 8.25 (m, 1H), 7.80 (s, 1H), 6.13 (d, 1H), 4.59 (m, 1H), 4.49 (m, 3H), 4.39 (m, 1H), 4.21 (m, 1H), 4.13 (m, 3H), 3.81 (s, 3H), 3.36 (s, 3H), 2.16 (m, 2H).

Example 6

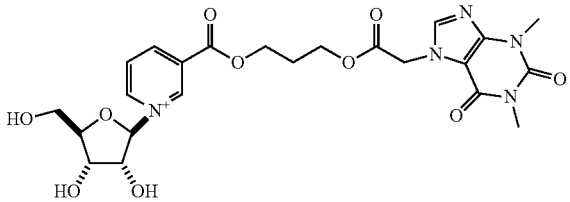

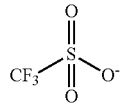

Compound 6

1-((2R,3R,4S,5R)-3,4-dihydroxy-5-(hydroxymethyl)
tetrahydrofuran-2-yl)-3-((3-(2-(1,3-dimethyl-2,6-
dioxo-1,2,3,6-tetrahydro-7H-purin-7-yl)acetoxy)
propoxy)carbonyl)pyridin-1-ium
trifluoromethanesulfonate

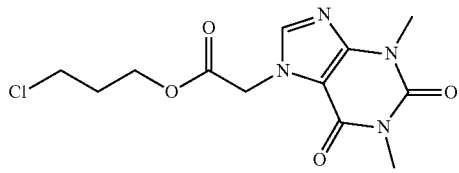 [SMILES: Cn1c(=O)c2c(ncn2CC(=O)OCCCCl)n(C)c1=O]

3-chloropropyl yl)acetate 2-(1,3-dimethyl-2,6-di-
oxo-1,2,3,6-tetrahydro-7H-purin-7-yl)acetate 2-(1,3-dimethyl-2,6-dioxo-1,2,3,6-tetrahydro-7H-purin-7-yl)acetic acid (2.40 g, 10.1 mmoles) was added to a 200 mL one necked 24/40 round bottomed flask with a magnetic stir bar and a 24/40 rubber septum. The flask was evacuated and placed under argon. Chloroform (25 mL) was added via syringe, then thionyl chloride (3.44 g, 29 mmoles) was added via syringe dropwise. A catalytic amount of dry DMF (1 mL) was then added cautiously and this mixture was heated gently in a 60° C. oil bath. After 1 hour, The reaction was concentrated in vacuo and coevaporated with chloroform (25 mL), giving an orange glass. More chloroform (25 mL) was added to dissolve the glass and 3-chloropropanol (1.02 g, 10.8 mmoles) was added via syringe. Triethylamine (2.04 g, 20.2 mmoles) was added via syringe and during the latter part of the addition an exotherm was noted and the color deepened to a dark orange. The reaction was allowed to stir at room temperature for 48 hours then quenched with saturated sodium bicarbonate (50 mL). The layers were separated and the organic phase dried over sodium sulfate, decanted and concentrated in vacuo, giving 3.6 g of crude product. This was purified using silica gel (40 g) and eluted with DCM then EtOAc. This gave 1.90 g (60%) product.

LRMS (ESI)$^+$ m/z: 315.

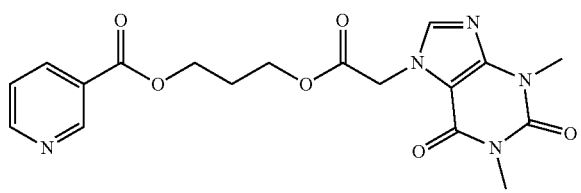 [SMILES: Cn1c(=O)c2c(ncn2CC(=O)OCCCOC(=O)c2cccnc2)n(C)c1=O]

3-(2-(1,3-dimethyl-2,6-dioxo-1,2,3,6-tetrahydro-7H-purin-7-yl)acetoxy)propyl nicotinate was prepared from the above chloride in a manner similar to 3-(2-(3,7-dimethyl-2,6-dioxo-2,3,6,7-tetrahydro-1H-purin-1-yl)acetoxy)propyl nicotinate, except that once finished, the reaction was concentrated in vacuo, dissolved in DCM ad filtered to give a glass, 2.77 g of crude product. This was purified utilizing silica gel (30 g) and DCM to 4% MeOH/DCM as eluent. The collected fractions gave 1.90 g of product upon concentration.

LRMS (ESI)$^+$ m/z: 402

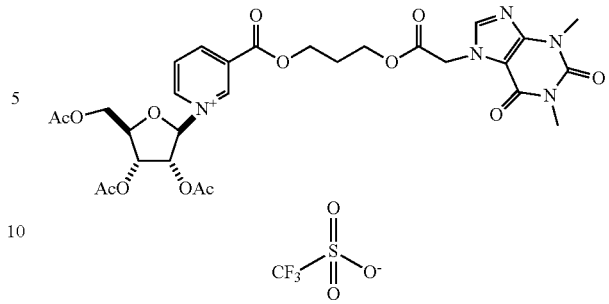

1-((2R,3R,4R,5R)-3,4-diacetoxy-5-(acetoxymethyl)tetrahydrofuran-2-yl)-3-((3-(2-(1,3-dimethyl-2,6-dioxo-1,2,3,6-tetrahydro-7H-purin-7-yl)acetoxy)propoxy)carbonyl)pyridin-1-ium trifluoromethanesulfonate was prepared in a manner similar to 1-((2R,3R,4R,5R)-3,4-di acetoxy-5-(acetoxymethyl)tetrahydrofuran-2-yl)-3-((2-(1,3-dimethyl-2,6-dioxo-1,2,3,6-tetrahydro-7H-purin-7-yl)ethoxy)carbonyl)pyridin-1-ium trifluoromethanesulfonate, except that the reaction required 2 hours to complete. 3-(2-(1,3-dimethyl-2,6-dioxo-1,2,3,6-tetrahydro-7H-purin-7-yl)acetoxy)propyl nicotinate (1.90 g, 4.73 mmoles) was reacted with 13-D-ribofuranose-1,2,3,5-tetraacetate (1.51 g, 4.73 mmoles) in dry dioxane (24 mL) and trimethylsilyltrifluorosulfonate (2.32 g, 10.4 mmoles) was added dropwise. Workup as before gave 4.32 g (113%) of crude product.

LRMS (ESI)$^+$ m/z: 660.

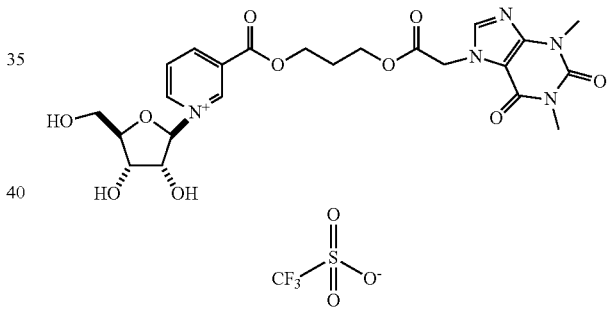

1-((2R,3R,4S,5R)-3,4-dihydroxy-5-(hydroxymethyl)
tetrahydrofuran-2-yl)-3-((3-(2-(1,3-dimethyl-2,6-
dioxo-1,2,3,6-tetrahydro-7H-purin-7-yl)acetoxy)
propoxy)carbonyl)pyridin-1-ium
trifluoromethanesulfonate Prepared in a manner similar to 1-((2R,3R,4S,5R)-3,4-dihydroxy-5-(hydroxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate.

1-((2R,3R,4R,5R)-3,4-diacetoxy-5-(acetoxymethyl)tetrahydrofuran-2-yl)-3-((3-(2-(1,3-dimethyl-2,6-dioxo-1,2,3,6-tetrahydro-7H-purin-7-yl)acetoxy)propoxy)carbonyl)pyridin-1-ium trifluoromethanesulfonate (3.83 g, 4.73 mmoles) was reacted in the cold (2-6° C.) with methanolic HCl for 18 hours. Precipitation by addition of MTBE (120 mL) was followed by decantation, dissolution in a minimum of cold methanol and reprecipitation with MTBE (2×) and the resulting residue was placed under high vacuum to give 1.99 g (61.9%) of crude product. This was purified using silica gel (30 g) and DCM to 20% methanol/DCM as eluent to give 0.665 g of purified product.

LRMS (ESI)+ m/z 534; $^1$H NMR (D$_2$O) δ 9.96 (1H, s), 9.30 (1H, d), 9.07 (1H, d), 8.29 (1H, d of d), 7.98 (1H, s), 6.23 (1H, d), 5.19 (2H, s), 4.48-4.44 (2H, m), 4.41-4.38 (4H, m), 4.44 (1H, t), 4.02 (1H, d of d), 3.86 (1H, d of d), 3.51 (3H, s), 3.21 (3H, s), 2.16 (2H, m).

Example 6P

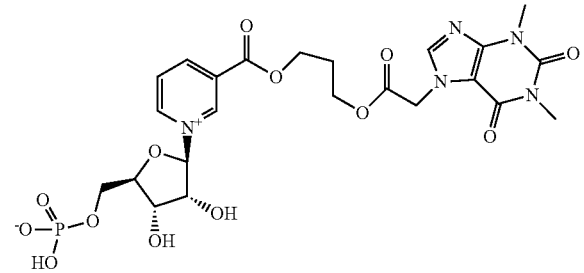

Compound 6P ((2R,3S,4R,5R)-5-(3-((3-(2-(1,3-dimethyl-2,6-dioxo-1,2,3,6-tetrahydro-7H-purin-7-yl)acetoxy)propoxy)carbonyl)pyridin-1-ium-1-yl)-3,4-dihydroxytetrahydrofuran-2-yl)methyl hydrogen phosphate This is prepared using a modification of the procedure for the synthesis of Compound 9P.

Example 7

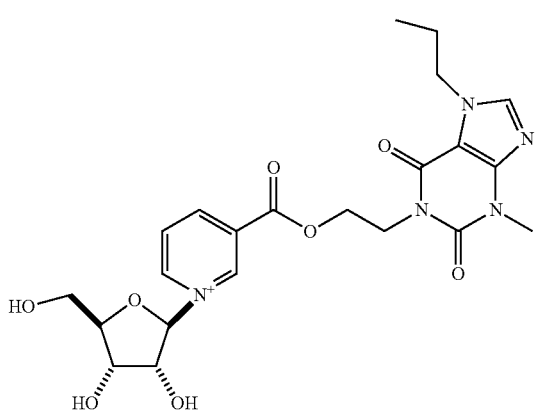

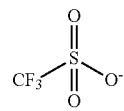

Compound 7

1-((2R,3R,4S,5R)-3,4-dihydroxy-5-(hydroxymethyl)tetrahydrofuran-2-yl)-3-((2-(3-methyl-2,6-dioxo-7-propyl-2,3,6,7-tetrahydro-1H-purin-1-yl)ethoxy)carbonyl)pyridin-1-ium trifluoromethanesulfonate

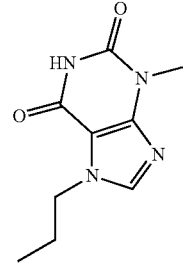

3-methyl-7-propyl-3,7-dihydro-1H-purine-2,6-dione was synthesized as follows. 3-methylxanthine (15.0 g, 90.3 mmoles) and potassium carbonate (crushed, 12.48 g, 90.3 mmoles) were combined in a 200 mL one necked round bottomed flask with a magnetic stir bar and a 24/40 rubber septum and the contents placed under argon. Dry DMF (120 mL) was added via syringe and the reaction heated in a 70° C. oil bath for 10 minutes. The 1-iodopropane was added dropwise over 10 minutes to the reaction mixture, after 1 hour another 1.75 g (10.3 mmoles) of 1-iodopropane was added dropwise, then after 40 minutes another 1.2 g (8.7 mmoles) of crushed potassium carbonate was added. After another 1 hour, another 1.00 g (7.24 mmoles) of crushed potassium carbonate was added and the reaction was continued in the 70° C. oil bath for 18 hours. The reaction mixture was removed from the oil bath and filtered while warm, the filtrate was concentrated in vacuo giving a white solid. This solid was washed with DMF, the solid was then kept under high vacuum prior to recrystallizing the product from ethanol/water. This gave 8.28 g (44% yield) of product.

LRMS (ESI)+ m/z 209.

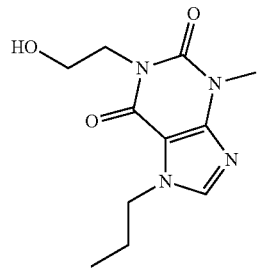 [SMILES: CCCn1cnc2c1c(=O)n(CCO)c(=O)n2C]

1-(2-hydroxyethyl)-3-methyl-7-propyl-3,7-dihydro-1H-purine-2,6-dione was synthesized in a manner similar to 1-(2-hydroxyethyl)-3,7-dimethyl-3,7-dihydro-1H-purine-2,6-dione.

3-methyl-7-propyl-3,7-dihydro-1H-purine-2,6-dione (6.24 g, 30 mmoles) was combined with potassium carbonate (crushed, 4.14 g, 30 mmoles), dry DMF (60 mL) was added and this was heated in a 100° C. oil bath for 2 hours. The 2-iodoethanol (5.16 g, 30 mmoles) was added dropwise to the room temperature reaction mixture over 10 minutes. After minutes, it was placed back into the 100° C. oil bath and heated for another 1 hour. Another g (5.2 mmoles) of 2-iodoethanol was added to the hot reaction dropwise. The reaction was heated for another 2 hours and then hot filtered and the filtrate was concentrated in vacuo. The residue was co-evaporated with toluene (3×30 mL) giving a white solid, 3.31 g (43.8% yield).

LRMS (ESI)$^+$ m/z 253.

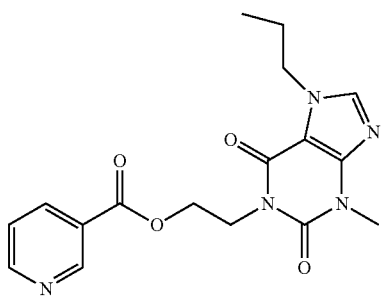 [SMILES: CCCn1cnc2c1c(=O)n(CCOC(=O)c1cccnc1)c(=O)n2C]

2-(3-methyl-2,6-dioxo-7-propyl-2,3,6,7-tetrahydro-1H-purin-1-yl)ethyl nicotinate was prepared in a manner similar to 2-(1,3-dimethyl-2,6-dioxo-1,2,3,6-tetrahydro-7H-purin-7-yl)ethyl nicotinate. The xanthine (3.23 g, 12.8 mmoles), nicotinic acid (1.61 g, 13.1 mmoles), 1-(3-Dimethylaminopropyl)-3-ethylcarbodiimide hydrochloride (2.58 g, 13.44 mmoles) and dimethylaminopyridine (0.313 g, 2.56 mmoles) were combined and DCM (30 mL) added. The reaction was stirred and briefly heated to reflux while under argon (5 minutes) and then allowed to stir at room temperature. An additional 0.5 g (2.61 mmoles) of 1-(3-Dimethylaminopropyl)-3-ethylcarbodiimide hydrochloride was added followed by another 0.22 g (0.87 mmoles) of the xanthine. After another 2.5 hours, saturated sodium bicarbonate (30 mL) was added and the biphasic reaction stirred for 10 minutes. The layers were separated, the organic phase re-washed three more times with the bicarbonate solution. Subsequent drying over sodium sulfate, decantation and concentration in vacuo gave 4.91 g (107% yield) of a glass.

LRMS (ESI)$^+$ m/z. 358

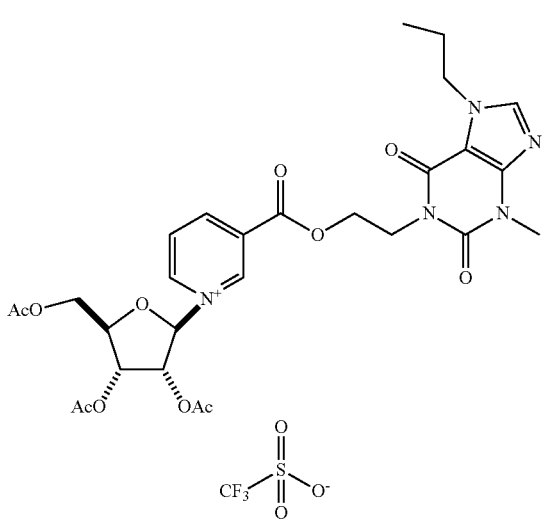

1-((2R,3R,4R,5R)-3,4-diacetoxy-5-(acetoxymethyl)tetrahydrofuran-2-yl)-3-((2-(3-methyl-2,6-dioxo-7-propyl-2,3,6,7-tetrahydro-1H-purin-1-yl)ethoxy)carbonyl)pyridin-1-ium trifluoromethanesulfonate was prepared in a similar fashion to 1-((2R,3R,4R,5R)-3,4-diacetoxy-5-(acetoxymethyl)tetrahydrofuran-2-yl)-3-((2-(1,3-dimethyl-2,6-dioxo-1,2,3,6-tetrahydro-7H-purin-7-yl)ethoxy)carbonyl)pyridin-1-ium trifluoromethanesulfonate. 2-(3-methyl-2,6-dioxo-7-propyl-2,3,6,7-tetrahydro-1H-purin-1-yl)ethyl nicotinate (4.57 g, 12.8 mmoles) and β-D-ribofuranose-1,2,3,5-tetraacetate (4.28 g, 13.4 mmoles) were placed in a 200 mL one necked round bottomed flask under argon with a magnetic stir bar and 24/40 rubber septum. Dry dioxane (24 mL) was added via syringe followed by trimethylsilyl trifluoromethanesulfonate (3.13 g, 14.1 mmoles) dropwise via syringe. After stirring at room temperature for 18 hours, saturated sodium bicarbonate (20 mL) and DCM (40 mL) were added and this was stirred for 10 minutes. The layers were separated and the lower organic phase dried over sodium sulfate, decanted and concentrated in vacuo to give a yellow foam, 10.22 g 104% yield.

LRMS (ESI)$^+$ m/z 616

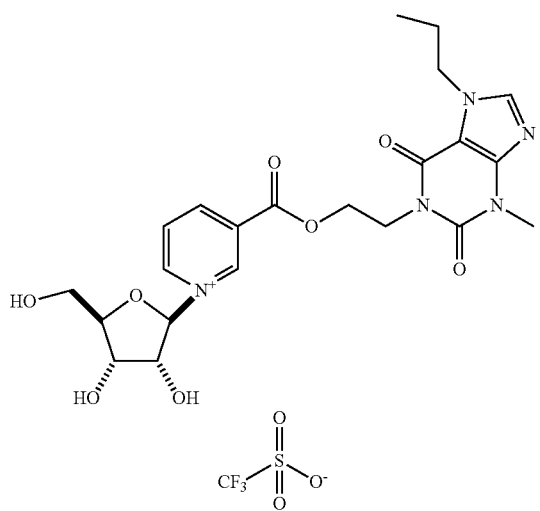

1-((2R,3R,4S,5R)-3,4-dihydroxy-5-(hydroxymethyl)tetrahydrofuran-2-yl)-3-((2-(3-methyl-2,6-dioxo-7-propyl-2,3,6,7-tetrahydro-1H-purin-1-yl)ethoxy)carbonyl)pyridin-1-ium trifluoromethanesulfonate Prepared in a manner similar to 1-((2R,3R,4S,5R)-3,4-dihydroxy-5-(hydroxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate The cold HCl in methanol solution was prepared by cautious addition of acetyl chloride (6.03 g, 76.8 mmoles) to cold dry methanol (50 mL) under argon over 10 minutes. This solution was added to the cold foam of 1-((2R,3R,4R,5R)-3,4-diacetoxy-5-(acetoxymethyl)tetrahydrofuran-2-yl)-3-((2-(3-methyl-2,6-dioxo-7-propyl-2,3,6,7-tetrahydro-1H-purin-1-yl)ethoxy)carbonyl)pyridin-1-ium trifluoromethanesulfonate (9.80 g, 12.8 mmoles) and the resulting solution was stirred in an ice water bath for 10 minutes prior to placing it in the refrigerator (5° C.) for 18 hours. MTBE (120 mL) was added, resulting in the precipitation of the product. The solvents were decanted, the thick syrup dissolved in a minimum of cold methanol and MTBE was again used to precipitate the product. This was repeated two more times until a solid was obtained, which was dried in vacuo, giving 4.55 g (55.6% yield) of the product.

LRMS (ESI)+ m/z 490; $^1$H NMR (D$_2$O) δ 9.75 (1H, s), 9.28 (1H, d), 9.01 (1H, d), 8.27 (1H, m), 7.94 (1H, s), 6.22 (1H, d), 4.78-4.74 (1H, m), 4.70-4.63 (1H, m), 4.44-4.43 (1H, t), 4.41-4.33 (3H, m), 4.30 (1H, t), 4.12 (2H, t), 3.83 (1H, d of d), 3.77 (1H, d of d), 3.45 (3H, s), 1.62 (2H, m), 0.71 (3H, t).

Example 7P

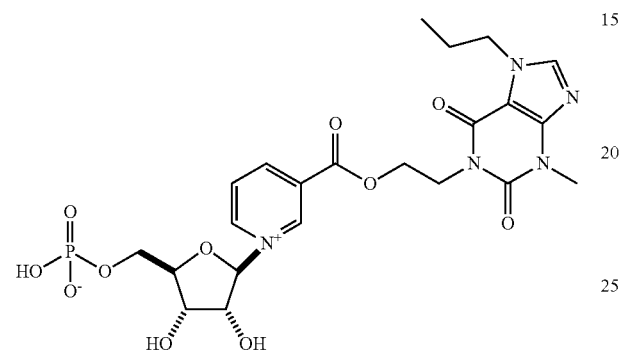

Compound 7P ((2R,3 S,4R,5R)-3,4-dihydroxy-5-(3-((2-(3-methyl-2,6-dioxo-7-propyl-2,3,6,7-tetrahydro-1H-purin-1-yl)ethoxy)carbonyl)pyridin-1-ium-1-yl)tetrahydrofuran-2-yl)methyl hydrogen phosphate 1-((2R,3R,4 S,5R)-3,4-dihydroxy-5-(hydroxymethyl)tetrahydrofuran-2-yl)-3-((2-(3-methyl-2,6-dioxo-7-propyl-2,3,6,7-tetrahydro-1H-purin-1-yl)ethoxy)carbonyl)pyridin-1-ium trifluoromethanesulfonate (2.00 g, 3.12 mmoles) was placed into a 100 mL one necked round bottomed flask with a magnetic stir bar under argon. TMP (12 mL) was added via syringe and the tan heterogeneous solution was cooled with an ice water bath for 10 minutes. The reaction mixture was degassed and placed under argon. Phosphorous oxychloride (0.960 g, 6.26 mmoles) was added dropwise over 4 minutes. After 7.5 hours, water (1.65 mL, 91.7 mmoles) was added cautiously, dropwise over 10 minutes. The reaction was stirred in the cold bath for minutes then placed into a refrigerator (5° C.) overnight. Triethylamine (2.62 mL, 1.90 g, 18.8 mmoles) was added to isopropyl alcohol (175 mL) in a 250 mL Erlenmeyer flask which was cooled with an ice water bath. After 10 minutes, the cold reaction mixture was added dropwise to the isopropyl alcohol solution over 10 minutes. This gave a precipitate. After stirring for 1 h, this solution was filtered and the solid was washed with isopropyl alcohol, then MTBE. The solid was dried, giving 1.43 g of crude product. This was purified by using reverse phase chromatography in a similar manner to ((2R,3S,4R,5R)-5-(3-((3-(3,7-dimethyl-2,6-dioxo-2,3,6,7-tetrahydro-1H-purin-1-yl)propoxy)carbonyl)pyridin-1-ium-1-yl)-3,4-dihydroxytetrahydrofuran-2-yl)methyl hydrogen phosphate.

LRMS (ESI)+ m/z. 570.1

Example 8

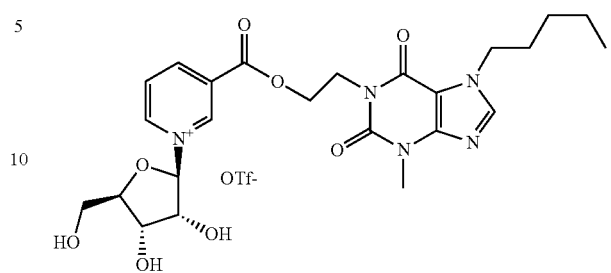

Compound 8

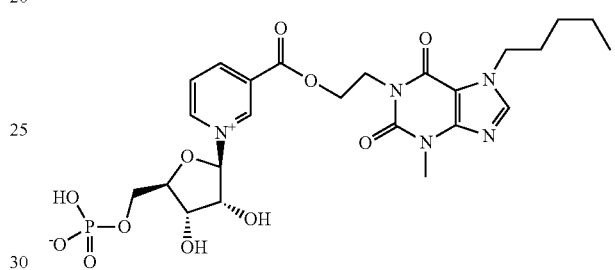

Compound 8P

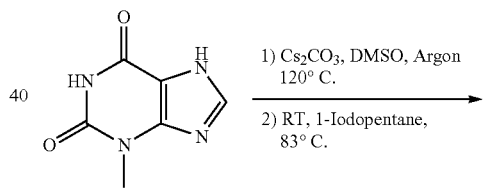

1) Cs$_2$CO$_3$, DMSO, Argon 120° C.

2) RT, 1-Iodopentane, 83° C.

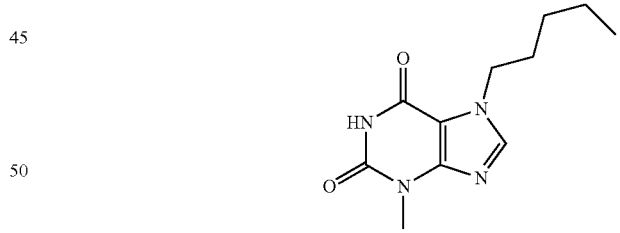

3-Methyl-7-pentyl xanthine was synthesized as follows. 3-Methylxanthine (2.00 g, 12.0 mmoles) and Cesium carbonate (3.92 g, 12.03 mmoles) were placed into a 100 mL one necked round bottomed flask with an egg shaped magnetic stir bar and placed under argon. DMSO (25 mL) was added via syringe and the reaction mixture was degassed and placed under argon then stirred. It was placed into a 120° C. oil bath for 3 hours. The reaction was removed from the heating bath and cooled to room temperature. 1-Iodopentane (1.57 mL, 2.38 g) was added dropwise over a 3 minute period. The reaction was placed into an 83° C. oil bath for 30 minutes. Another 0.313 mL (0.5 g) of 1-Iodopentane was added at this time, and the reaction was allowed to cool to room temperature. After 1.5 hours, methyl t-butylether (10 mL) and dichloromethane (70 mL) were added, giving solid and liquid phases. This was filtered and the filtrate concentrated in vacuo, giving a thick liquid. This was added as a stream to water (150 mL) producing a solid. After 30 minutes, the solid was isolated by filtration, washed with water, and dried in vacuo. The solid was recrystallized from ethanol/water to give 1.68 g of product, a 59% yield.

$^1$HNMR (DMSO-d$_6$) δ 11.1 (s, 1H), 8.05 (s, 1H), 4.20 (t, 2H), 3.35 (s, 3H), 1.77 (quint, 2H), 1.28 (m, 2H), 1.19 (m, 2H), 0.85 (t, 3H); LRMS (ESI)$^+$ m/z 237.

1-Hydroxyethyl-7-Pentyl-3-Methyl xanthine

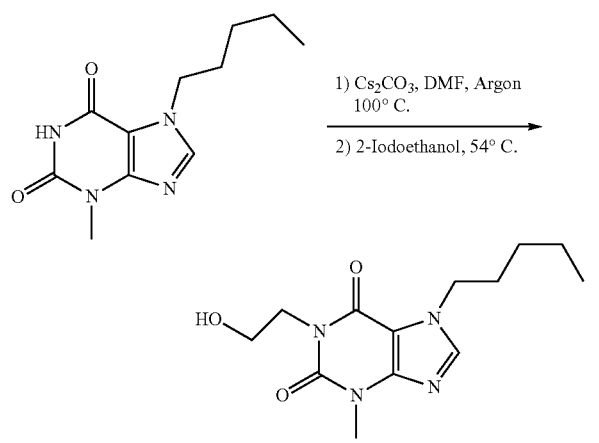

3-Methyl-7-pentyl xanthine (3.50 g, 14.8 mmoles) and Cs$_2$CO$_3$ (6.08 g, 18.7 mmoles) were placed into a 100 mL one necked round bottomed flask with an egg shaped magnetic stir bar and placed under argon. DMSO (25 mL) was added via syringe and the reaction mixture was degassed and placed under argon then stirred. It was placed into a 120° C. oil bath for 3 hours. The reaction was removed from the heating bath and cooled to room temperature. 2-Iodoethanol (1.57 mL, 2.38 g) was added dropwise over a 3 minute period. The reaction was placed into an 83° C. oil bath for 30 minutes. Another 0.313 mL (0.5 g) of 2-Iodoethanol was added at this time, and the reaction was allowed to cool to room temperature. After 1.5 hours, methyl t-butylether (10 mL) and dichloromethane (70 mL) were added, giving solid and liquid phases. This was filtered and the filtrate concentrated in vacuo, giving a thick liquid. This was added as a stream to water (150 mL) producing a solid. After 30 minutes, the solid was isolated by filtration, washed with water, and dried in vacuo. The solid was recrystallized from ethanol/water to give 1.68 g of product, a 59% yield.

$^1$HNMR (DMSO-d$_6$) δ 11.1 (s, 1H), 8.05 (s, 1H), 4.20 (t, 2H), 3.35 (s, 3H), 1.77 (quint, 2H), 1.28 (m, 2H), 1.19 (m, 2H), 0.85 (t, 3H). LRMS (ESI)$^+$ m/z 281.

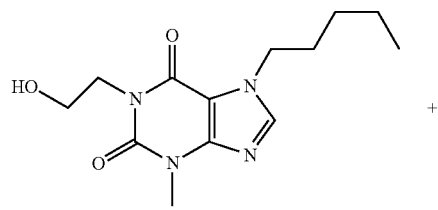

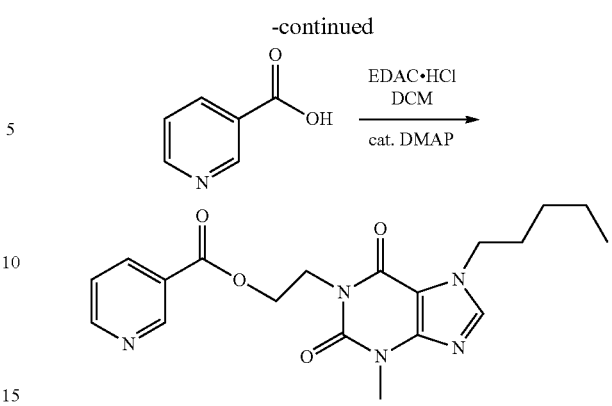

The reaction was run using dichloromethane as solvent, according to the procedure described for hydroxymethyl dimethyl xanthine, with 1-Hydroxyethyl-7-Pentyl-3-Methyl xanthine (3.90 g, 13.9 mmoles), nicotinic acid (1.80 g, 14.6 mmoles), EDAC·HCl (2.95 g, 15.4 mmoles), and dimethylaminopyridine (0.170 g, 1.39 mmoles).

Yield=87%; MS+=386.

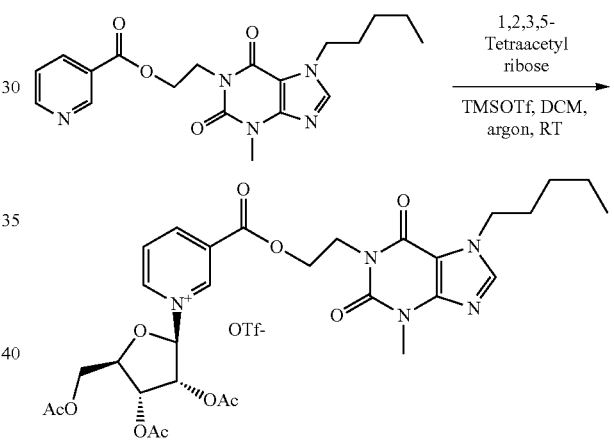

The reaction was run according to the procedure described for 1-((2R,3R,4R,5R)-3,4-di acetoxy-5-(acetoxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate, with 2-(3-methyl-2,6-dioxo-7-pentyl-2,3,6,7-tetrahydro-1H-purin-1-yl)ethyl nicotinate (4.66 g, 12.10 mmoles); 1,2,3,5-Tetraacetyl ribose (4.04 g, 12.70 mmoles), and Trimethylsilyltrifluoromethylsulfonate (2.96 g, 13.31 mmoles).

Yield=95%; LRMS (ESI)$^+$ m/z 644.6.

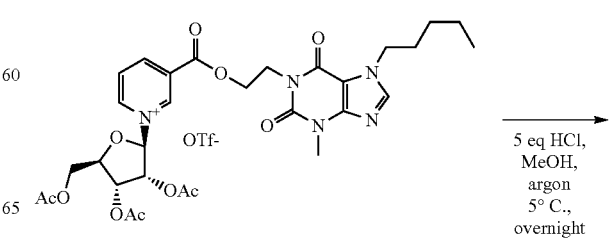

-continued

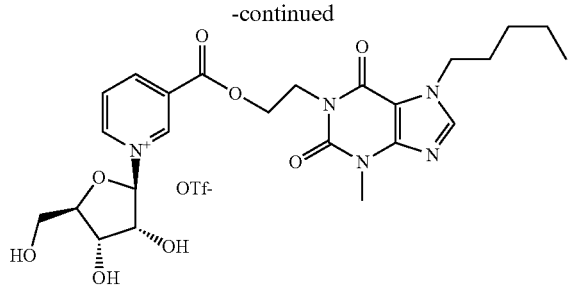

Compound 8. This reaction was run in a similar manner to that which was used to prepare 1-((2R,3R,4S,5R)-3,4-dihydroxy-5-(hydroxymethyl)tetrahydrofuran-2-yl)-3-((3-(2-(3,7-dimethyl-2,6-dioxo-2,3,6,7-tetrahydro-1H-purin-1-yl)acetoxy)propoxy)carbonyl)pyridin-1-ium trifluoromethanesulfonate, with 1-((2R,3R,4R,5R)-3,4-diacetoxy-5-(acetoxymethyl)tetrahydrofuran-2-yl)-3-((2-(3-methyl-2,6-dioxo-7-pentyl-2,3,6,7-tetrahydro-1H-purin-1-yl)ethoxy)carbonyl)pyridin-1-ium (9.00 g, 11.35 mmoles) and acetyl chloride (6.60 g, 84.0 mmoles).

Yield=69%; LRMS (ESI)+ m/z 518.22.

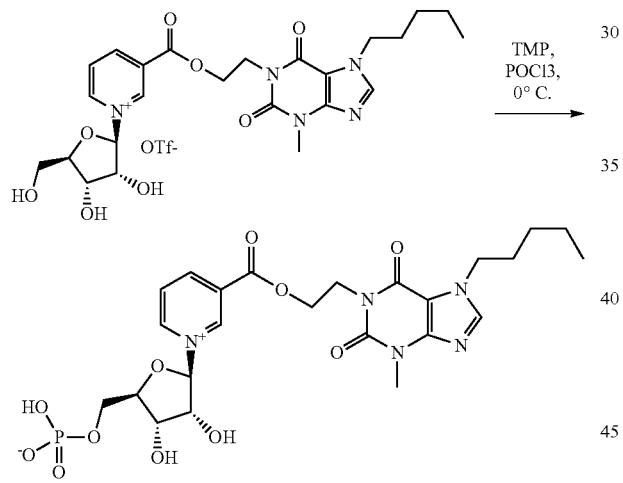

Compound 8P. This reaction was run in a similar manner to that which was used to prepare ((2R,3 S,4R,5R)-5-(3-((2-(3,7-dimethyl-2,6-dioxo-2,3,6,7-tetrahydro-1H-purin-1-yl)ethoxy)carbonyl)pyridin-1-ium-1-yl)-3,4-dihydroxytetrahydrofuran-2-yl)methyl hydrogen phosphate, with 1-((2R,3R,4S,5R)-3,4-dihydroxy-5-(hydroxymethyl)tetrahydrofuran-2-yl)-3-((2-(3-methyl-2,6-dioxo-7-pentyl-2,3,6,7-tetrahydro-1H-purin-1-yl)ethoxy)carbonyl)pyridin-1-ium (3.00 g, 4.50 mmoles) and phosphorous oxychloride (1.38 g, 9.00 mmoles). Yield=25.2%.

$^1$H NMR (D$_2$O) δ 9.43 (s, 1H), 9.33 (d, 1H), 8.97 (d, 1H), 8.27 (d of d, 1H), 7.90 (s, 1H), 6.15 (d, 1H), 4.71 (m, 1H), 4.64 (m, 1H), 4.55 (bt, 1H), 4.48 (t, 1H), 4.38 (m, 3H), 4.14 (bt, 2H), 4.08 (m, 2H), 3.43 (s, 3H), 1.62 (m, 2H), 1.10 (m, 4H), 0.71 (bt, 3H); 31 P NMR (D$_2$O) δ −0.26

LRMS (ESI)+ m/z 598.0.

Example 9

Compound 9

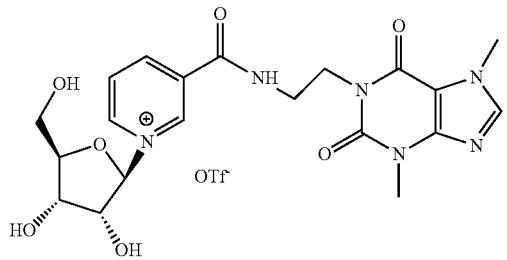 [SMILES: Cn1cnc2c1c(=O)n(CCNC(=O)c1ccc[n+]([C@@H]3O[C@H](CO)[C@@H](O)[C@H]3O)c1)c(=O)n2C]

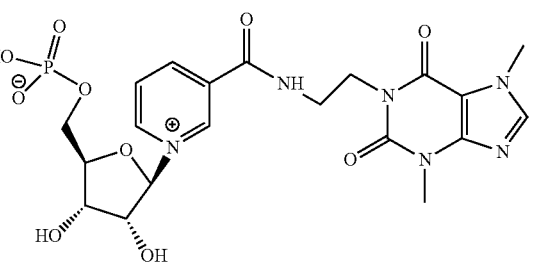

Compound 9P ((2R,3S,4R,5R)-5-(3-((2-(3,7-dimethyl-2,6-dioxo-2,3,6,7-tetrahydro-1H-purin-1-yl)ethyl)carbamoyl)pyridin-1-ium-1-yl)-3,4-dihydroxytetrahydrofuran-2-yl)methyl hydrogen phosphate

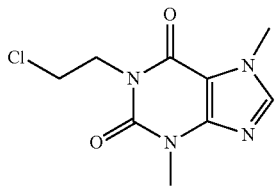 [SMILES: Cn1cnc2c1c(=O)n(CCCl)c(=O)n2C]

1-(2-chloroethyl)-3,7-dimethyl-3,7-dihydro-1H-purine-2,6-dione was synthesized as follows. 1-(2-Hydroxyethyl)-3,7-dimethyl-3,7-dihydro-1H-purine-2,6-dione (7.00 g, 31.25 mmoles) was added to a 500 mL 1 necked round bottomed flask and placed under argon. Dry dioxane (150 mL) was added via syringe and the heterogeneous solution was stirred. Triethylamine (3.48 g, 34.4 mmoles) was added then methanesulfonyl chloride 3.75 g, 32.8 mmoles) was added dropwise over 5 minutes. This reaction was heated in a 70° C. bath overnight (16 hours). The reaction was concentrated in vacuo and the resulting solid was washed with water, then dried in vacuo. The reaction was incomplete and the solid was placed into a 200 mL round bottomed flask, and dry dioxane added (25 mL). This was stirred and 0.35 g (3.46 mmoles) triethylamine and then methanesulfonyl chloride 0.38 g (3.32 mmoles) were added to the stirred reaction mixture. This was again heated in a 70° C. bath for 2 hours. The reaction was then concentrated in vacuo, and the solid washed with water and then MTBE and dried in vacuo, giving 6.12 g 80.9% yield of 1-(2-chloroethyl)-3,7-dimethyl-3,7-dihydro-1H-purine-2,6-dione.

LRMS (ESI)+ m/z 243.

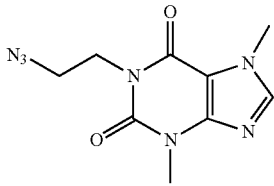 [SMILES: Cn1cnc2c1c(=O)n(CCN=[N+]=[N-])c(=O)n2C]

1-(2-azidoethyl)-3,7-dimethyl-3,7-dihydro-1H-purine-2,6-dione was synthesized as follows. 1-(2-chloroethyl)-3,7-dimethyl-3,7-dihydro-1H-purine-2,6-di one (6.12 g, 24.6 mmoles) and sodium azide (1.65 g, 25.3 mmoles) were placed into a 200 mL round bottomed flask equipped with a magnetic stir bar and dry DMF (30 mL) was added via syringe, the reaction was placed under argon in heated in a 120° C. oil bath for 1.5 hours. The reaction mixture was filtered hot and the filtrate was concentrated in vacuo to give a white solid, 6.30 g, 100% yield.

LRMS (ESI)+ m/z 250.1.

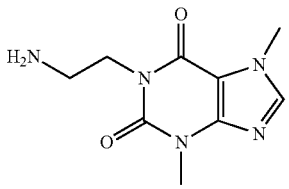 [SMILES: Cn1cnc2c1c(=O)n(CCN)c(=O)n2C]

1-(2-aminoethyl)-3,7-dimethyl-3,7-dihydro-1H-purine-2,6-dione was synthesized as follows. 1-(2-azidoethyl)-3,7-dimethyl-3,7-dihydro-1H-purine-2,6-dione (6.30 g, 25.3 mmoles) and triphenylphosphine (6.97 g, 26.6 mmoles) were placed into a 200 mL one necked round bottomed flask with a magnetic stir bar under argon. Dry THF (80 mL) was added and this was stirred. This was heated in a 50° C. water bath for one hour while it foamed. Water (4.77 g, 265 mmoles) was added to the reaction dropwise over 5 minutes and the water bath temperature increased to 75° C. After 1.5 hours the reaction was concentrated in vacuo, giving a gummy solid. The solid was treated with hot water until only a small amount of solid was present. It was hot filtered and the filtrate concentrated in vacuo, yielding 5.23 g of a slightly impure product. This was clean enough to use in the next reaction.

LRMS (ESI)+ m/z 224.

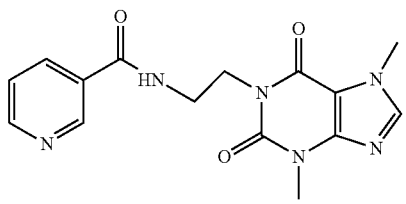 [SMILES: Cn1cnc2c1c(=O)n(CCNC(=O)c1cccnc1)c(=O)n2C]

N-(2-(3,7-dimethyl-2,6-dioxo-2,3,6,7-tetrahydro-1H-purin-1-yl)ethyl)nicotinamide was synthesized as follows. 1-(2-aminoethyl)-3,7-dimethyl-3,7-dihydro-1H-purine-2,6-dione (1.65 g, 7.40 mmoles), nicotinic acid (1.35 g, 10.97 mmoles) and 3-(3-Dimethylaminopropyl)-1-ethyl-carbodiimide hydrochloride (2.21 g, 11.53 mmoles) were placed into a 200 mL one necked round bottomed flask with a magnetic stir bar under argon. Dry dioxane (30 mL) was added via syringe and this was stirred. Triethylamine (1.10 g, 10.9 mmoles) was added via syringe and the reaction was stirred overnight at room temperature. The reaction mixture was concentrated in vacuo, dissolved in CHCl$_3$ and washed with saturated NaHCO$_3$ and saturated NaCl. The combined aqueous phases were back extracted with CHCl$_3$ which was combined with the prior organic phase. The organic phase was dried over Na$_2$SO$_4$, decanted and concentrated in vacuo to give 3.81 g of a glass. This was dissolved in DCM and purified utilizing 75 g of silica gel and a gradient of 0-20% methanol in DCM. The product fractions were collected and concentrated in vacuo to give 1.28 g of product a 52.7% yield.

LRMS (ESI)+ m/z 329.1.

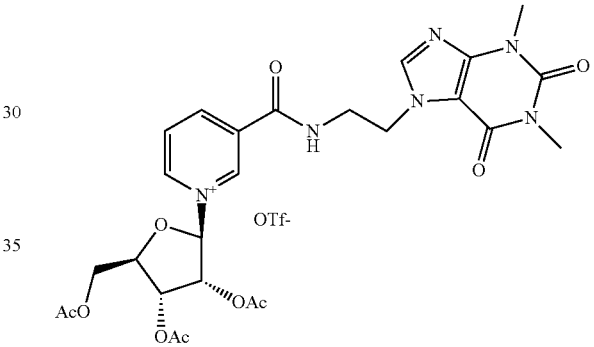

1-02R,3R,4R,5R)-3,4-diacetoxy-5-(acetoxymethyl)tetrahydrofuran-2-yl)-3-((2-(3,7-dimethyl-2,6-dioxo-2,3,6,7-tetrahydro-1H-purin-1-yl)ethyl)carbamoyl)pyridin-1-ium trifluoromethane sulfonate was synthesized as follows. N-(2-(3,7-dimethyl-2,6-dioxo-2,3,6,7-tetrahydro-1H-purin-1-yl) ethyl)nicotinamide (2.73 g, 8.22 mmoles) and 1,2,3,5-Tetraacetyl-b-D-ribofuranose (2.91 g, 9.16 mmoles) were added to a 500 mL one necked round bottomed flask along with a magnetic stir bar and placed under argon. Dry dioxane (30 mL) and DCM (45 mL) were added. Trimethylsilyltrifluoromethnesulfonate (2.14 g, 9.62 mmoles) was added dropwise to the stirred reaction over 3 minutes. The reaction was stirred for 6.5 hours at room temperature. Saturated NaHCO$_3$ (30 mL) was added and this was stirred for 5 minutes. The layers were separated and the organic phase washed with saturated NaCl solution (15 mL). The combined aqueous solutions were back extracted with DCM and the combined organic phases were dried over Na$_2$SO$_4$. The solution was decanted and concentrated in vacuo to give a quantitative yield of product. This material was carried on to the next reaction without further purification.

LRMS (ESI)+ m/z 587.2.

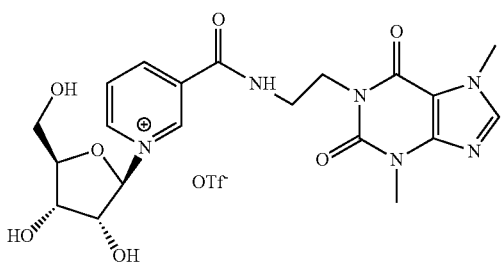 [SMILES: Cn1cnc2c1c(=O)n(CCNC(=O)c1ccc[n+]([C@@H]3O[C@H](CO)[C@@H](O)[C@H]3O)c1)c(=O)n2C]

1-((2R,3R,4S,5R)-3,4-dihydroxy-5-(hydroxymethyl)tetrahydrofuran-2-yl)-3-((2-(3,7-dimethyl-2,6-dioxo-2,3,6,7-tetrahydro-1H-purin-1-yl)ethyl)carbamoyl)pyridin-1-ium trifluoromethane sulfonate was synthesized as follows. Anhydrous methanol (30 mL) was added to a 100 mL one necked round bottomed flask with a magnetic stir bar under argon using a syringe. This was placed into an ice/water bath for 10 minutes and acetyl chloride (3.59 g, 45.7 mmoles) was added via syringe dropwise. 1-((2R,3R,4R,5R)-3,4-diacetoxy-5-(acetoxymethyl)tetrahydrofuran-2-yl)-3-((2-(3, 7-dimethyl-2,6-dioxo-2,3,6,7-tetrahydro-1H-purin-1-yl) ethyl)carbamoyl)pyridin-1-ium trifluoromethane sulfonate in a 200 mL one necked round bottomed flask with a magnetic stir bar under argon was placed into a −25° C. freezer for minutes. When the cold HO/methanol solution was ready (5 minutes after addition of the acetyl chloride) it was added in one portion to the cold foam of the starting material. This was stirred in the ice water bath for 10 minutes and placed into a refrigerator (5° C.) overnight (16 hours). The reaction was removed from the refrigerator and placed into an ice water bath and MTBE (150 mL) added as a slight stream to the mixture, forming a gum consisting of product. The solvents were decanted from the gum which was dissolved in methanol (30 mL) and another portion of MTBE was added with a similar result. After decantation, the gum was dissolved in methanol (30 mL) and this solution was added dropwise to well stirred MTBE (150 mL) which gave a nice solid, 3.65 g (72.7% yield) after drying.

LRMS (ESI)+ m/z. 461.2.

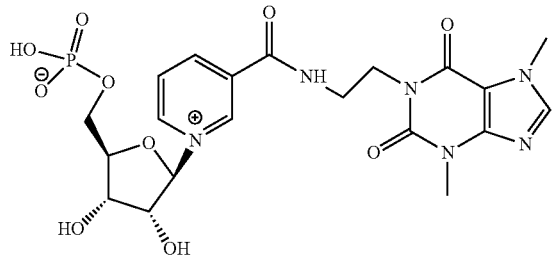 [SMILES: Cn1cnc2c1c(=O)n(CCNC(=O)c1ccc[n+]([C@@H]3O[C@H](COP(=O)([O-])O)[C@@H](O)[C@H]3O)c1)c(=O)n2C]

((2R,3S,4R,5R)-5-(3-((2-(3,7-dimethyl-2,6-dioxo-2,3,6, 7-tetrahydro-1H-purin-1-yl)ethyl)carbamoyl)pyridin-1-ium-1-yl)-3,4-dihydroxytetrahydrofuran-2-yl)methyl hydrogen phosphate was synthesized as follows. 1-((2R,3R,4S, 5R)-3,4-dihydroxy-5-(hydroxymethyl)tetrahydrofuran-2-yl)-3-((2-(3,7-dimethyl-2,6-dioxo-2,3,6,7-tetrahydro-1H-purin-1-yl)ethyl)carbamoyl)pyridin-1-ium trifluoromethane sulfonate (3.00 g, 4.91 mmoles) was placed into a 200 mL one necked round bottomed flask with a magnetic stir bar under argon, this flask was placed into an ice water bath. Dry, cold (refrigerator) TMP (15 mL) was added via syringe, giving a heterogeneous solution to which phosphorous oxychloride (1.51 g, 9.83 mmoles) was added dropwise via syringe over 8 minutes. After 4 hours triethylamine (0.248 g, 2.5 mmoles) was added dropwise. After 1 hours, water (2.65 g, 147 mmols) was added slowly dropwise to the cold reaction mixture. The reaction was stirred for 10 minutes in the cold bath then placed into a −25° C. freezer overnight. A solution of triethyl amine (2.73 g, 27.0 mmoles) in isopropyl alcohol (12 mL) was prepared and added dropwise to the cold reaction. This gave a heterogeneous solution with a pH of 3.0. After 30 minutes the solid was filtered out and washed with isopropyl alcohol (30 mL) then MTBE (20 mL). The solid was dried in vacuo, giving 4.46 g of crude product. A portion of this was purified using a 40 g reverse phase column with a gradient of 0 to 30% methanol in water. The appropriate fractions were collected and concentrated in vacuo and the resulting solid was lyophilized to give 0.530 g of product.

LRMS (ESI)+ m/z. 541.2.

Example 10

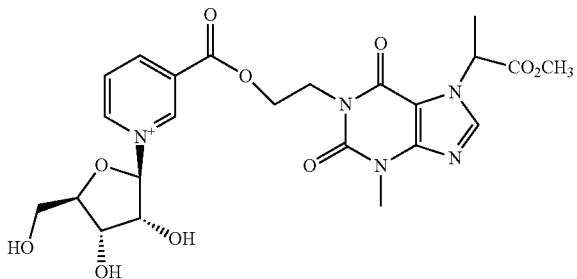 [SMILES: COC(=O)C(C)n1cnc2c1c(=O)n(CCOC(=O)c1ccc[n+]([C@@H]3O[C@H](CO)[C@@H](O)[C@H]3O)c1)c(=O)n2C]

Compound 10

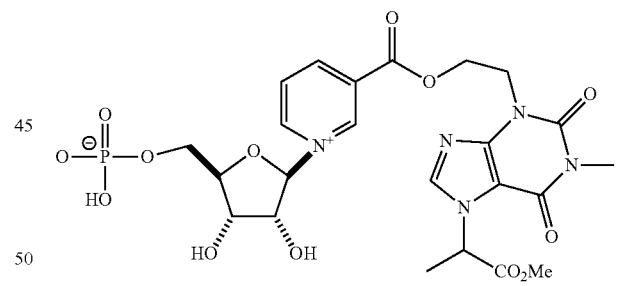

Compound 10P ((2R,3 S,4R,5R)-3,4-dihydroxy-5-(3-((2-(7-(1-methoxy-1-oxopropan-2-yl)-1-methyl-2,6-dioxo-1,2, 6,7-tetrahydro-3H-purin-3-yl)ethoxy)carbonyl)pyridin-1-ium-1-yl)tetrahydrofuran-2-yl)methyl hydrogen phosphate 3-methyl-3,7-dihydro-1H-purine-2,6-dione (8.00 g, 48.2 mmoles) and potassium carbonate (crushed, 6.66 g, 48.2 mmoles) were placed into a 200 mL one necked round bottomed flask along with a magnetic stir bar and placed under argon. Dry DMF (80 mL) was added and this heterogeneous reaction mixture was placed into a 100° C. oil bath for 2 hours. It was removed from the oil bath and placed into a room temperature water bath for 10 minutes. Potassium Iodide (crushed, 8.00 g, 48.2 mmoles) was added, then 2-chloromethylpropionate (5.90 g, 48.2 mmoles) was added dropwise to the stirred, cool reaction. This was stirred for 5 minutes the placed into the 100° C. oil bath and the reaction continued for 1.25 hours. The reaction was removed from the hot oil bath and cooled to room temperature. It was filtered and the filtrate concentrated in vacuo to give a solid. The solid was washed with MTBE and dried in vacuo. The solid was washed with water (20 mL), filtered and rinsed with more water. The solid was coevaporated with acetonitrile (20 mL) and dried in vacuo to give 7.80 g, 64.2% yield of product.

LRMS (ESI)+ m/z. 253.1.

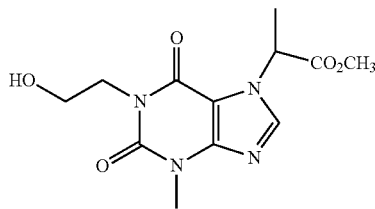 [SMILES: COC(=O)C(C)n1cnc2c1c(=O)n(CCO)c(=O)n2C]

methyl 2-(1-(2-hydroxyethyl)-3-methyl-2,6-dioxo-1,2,3,6-tetrahydro-7H-purin-7-yl)propanoate was synthesized as follows. methyl 2-(3-methyl-2,6-dioxo-1,2,3,6-tetrahydro-7H-purin-7-yl)propanoate (3.5 g, 13.9 mmoles) and potassium carbonate (crushed, 1.92 g, 13.9 mmoles) were placed into a 200 mL one necked round bottomed flask along with a magnetic stir bar and placed under argon. Dry DMF (35 mL) was added via syringe and the heterogeneous reaction was placed into an 85° C. oil bath for 1 hour. The reaction was cooled in an ice water bath for 5 minutes and 2-chloroethanol (1.12 g, 13.9 mmoles) was added dropwise over 3 minutes. It was then replaced into the 85° C. oil bath for 2 hours. It was removed from the oil bath and cooled to room temperature. Another portion of 2-chloroethanol (0.55 g) was added and the reaction continued in the 85° C. bath for overnight. The reaction was hot filtered and the filtrate concentrated in vacuo to give a glass. The glass was co evaporated with methanol and acetonitrile, giving 4.61 g of product which was used without further purification.

LRMS (ESI)+ m/z. 297.1.

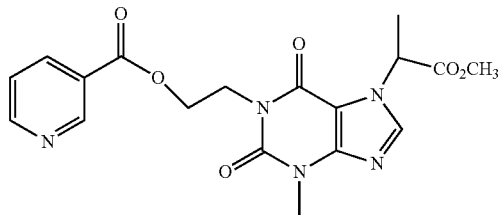 [SMILES: COC(=O)C(C)n1cnc2c1c(=O)n(CCOC(=O)c1cccnc1)c(=O)n2C]

2-(7-(1-methoxy-1-oxopropan-2-yl)-3-methyl-2,6-dioxo-2,3,6,7-tetrahydro-1H-purin-1-yl)ethyl nicotinate was synthesized as follows. methyl 2-(1-(2-hydroxyethyl)-3-methyl-2,6-dioxo-1,2,3,6-tetrahydro-7H-purin-7-yl) propanoate (4.61 g, 15.6 mmoles), nicotinic acid (1.92 g, 15.6 mmoles), 3-(3-Dimethylaminopropyl)-1-ethyl-carbodiimide hydrochloride (3.30 g, 17.2 mmoles) and dimethylaminopyridine (0.19 g, 1.56 mmoles) were combined in a 200 mL one necked round bottomed flask with a magnetic stir bar and placed under argon. DCM (40 mL) was added and the reaction stirred at room temperature. The reaction did not complete after 2 days and 2 more portions of 3-(3-Dimethylaminopropyl)-1-ethyl-carbodiimide hydrochloride were added (1.21 g and then 2 hours later another 1.0 g). The reaction was stirred for overnight and saturated NaHCO₃ (2×30 mL) was added to work it up. The organic phase was dried over Na₂SO₄, decanted and concentrated in vacuo to give a glass. The reaction had not completed and therefore another allotment of nicotinic acid (0.94 g, 7.64 mmoles), 3-(3-Dimethylaminopropyl)-1-ethyl-carbodiimide hydrochloride (1.65 g, 8.61 mmoles) and dimethylaminopyridine (0.133 g, 1.09 mmoles) were added to the residue and DCM (50 mL) added. After 1 hour the reaction was complete and saturated NaHCO₃ (4×15 mL) was used to wash the reaction mixture. The DCM solution was dried using sodium sulfate, decanted and concentrated in vacuo to give 6.12 g of crude product. This was purified using 50 g of Silica gel and a 0-2% MeOH DCM elution solvent. This gave 3.07 g of product, a 49% yield.

LRMS (ESI)+ m/z. 402.1.

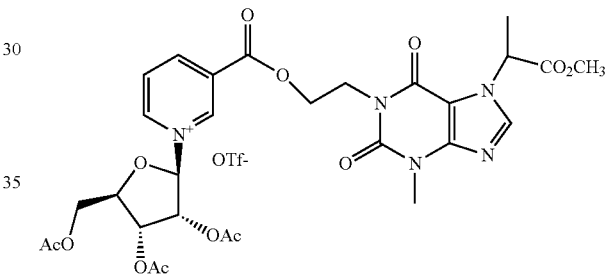

1-((2R,3R,4R,5R)-3,4-diacetoxy-5-(acetoxymethyl)tetrahydrofuran-2-yl)-3-((2-(7-(1-methoxy-1-oxopropan-2-yl)-3-methyl-2,6-dioxo-2,3,6,7-tetrahydro-1H-purin-1-yl) ethoxy)carbonyl)pyridin-1-ium trifluoromethane sulfonate was synthesized as follows. 2-(7-(1-m ethoxy-1-oxopropan-2-yl)-3-methyl-2,6-dioxo-2,3,6,7-tetrahydro-1H-purin-1-yl) ethyl nicotinate (3.07 g, 7.65 mmoles) and 1,2,3,5-Tetraacetyl-b-D-ribofuranose (2.56 g, 8.03 mmoles) were added to a 300 mL one necked round bottomed flask along with a magnetic stir bar and placed under argon. DCM (40 mL) was added and the reaction was stirred. Trimethylsilyltrifluoromethanesulfonate (1.87 g, 8.42 mmoles) was added dropwise to the stirred reaction over 3 minutes. After 4.5 hours the reaction had not completed and 1,2,3,5-Tetraacetyl-b-D-ribofuranose (0.200 g, 0.63 mmoles) and then trimethylsilyltrifluoromethanesulfonate (0.184 g, 0.83 mmoles) were added and the reaction was allowed to stir overnight. Saturated NaHCO₃ (2×20 mL) was used to wash the organic reaction mixture which was dried over sodium sulfate. The solution was decanted from the solid and concentrated in vacuo to give a quantitative yield of impure product.

LRMS (ESI)+ m/z. 598.2.

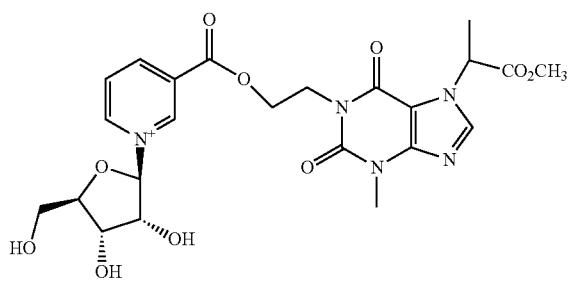 [SMILES: COC(=O)C(C)n1cnc2c1c(=O)n(CCOC(=O)c1ccc[n+]([C@@H]3O[C@H](CO)[C@@H](O)[C@H]3O)c1)c(=O)n2C]

1-((2R,3R,4S,5R)-3,4-dihydroxy-5-(hydroxymethyl)tetrahydrofuran-2-yl)-3-((2-(7-(1-methoxy-1-oxopropan-2-yl)-3-methyl-2,6-dioxo-2,3,6,7-tetrahydro-1H-purin-1-yl)ethoxy)carbonyl)pyridin-1-ium trifluoromethanesulfonate was synthesized as follows. 1-((2R,3R,4R,5R)-3,4-diacetoxy-5-(acetoxymethyl)tetrahydrofuran-2-yl)-3-((2-(7-(1-methoxy-1-oxopropan-2-yl)-3-methyl-2,6-dioxo-2,3,6,7-tetrahydro-1H-purin-1-yl)ethoxy)carbonyl)pyridin-1-ium trifluoromethane sulfonate (6.51 g, 7.65 mmoles) in a 200 mL one necked round bottomed flask along with a magnetic stir bar under argon was placed into a −25° C. freezer. Anhydrous methanol (40 mL) was added to a 100 mL one necked round bottomed flask with a magnetic stir bar under argon using a syringe. This was placed into an ice/water bath for 10 minutes and acetyl chloride (3.82 g, 48.7 mmoles) was added via syringe dropwise over 5 minutes. This solution was added in one portion to the cold flask containing the substrate and it was stirred in an ice water bath for 10 minutes before placing it in a refrigerator at 5° C. overnight. The resulting solution was added to a well stirred solution of MTBE (350 mL0 in a 500 mL erlenmyler flask over a 30 minute period. This gave a nice solid which was allowed to settle, and washed with two portions of MTBE, the resulting solid was placed into a 300 mL one necked round bottomed flask and placed under high vacuum, giving 4.72 g of product.

LRMS (ESI)$^+$ m/z. 534.2.

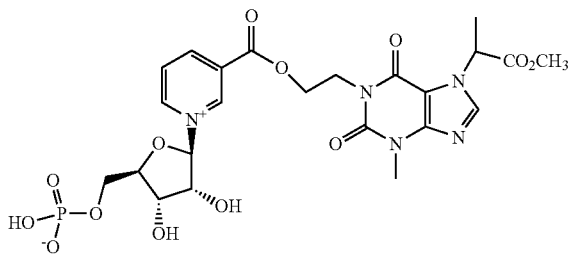

((2R,3S,4R,5R)-3,4-dihydroxy-5-(3-((2-(7-(1-methoxy-t-oxopropan-2-yl)-3-methyl-2,6-dioxo-2,3,6,7-tetrahydro-1H-purin-1-yl)ethoxy)carbonyl)pyridin-1-ium-1-yl)tetrahydrofuran-2-yl)methyl hydrogen phosphate was synthesized as follows. 1-((2R,3R,4 S,5R)-3,4-dihydroxy-5-(hydroxymethyl)tetrahydrofuran-2-yl)-3-((2-(7-(1-m ethoxy-1-oxopropan-2-yl)-3-methyl-2,6-dioxo-2,3,6,7-tetrahydro-1H-purin-1-yl)ethoxy)carbonyl)pyridin-1-ium trifluoromethanesulfonate (4.00 g, 5.85 mmoles) was placed into a 200 mL one necked round bottomed flask and a magnetic stir bar added. This was placed under argon and placed into an ice water cold bath. Dry TMP (24 mL) was added via syringe and this was stirred for 10 minutes giving a homogeneous light yellow solution. Phosphorous oxychloride (1.79 g, 11.70 mmoles) was added dropwise over 6 minutes. After 3.5 hours, triethylamine (0.301 mg, 2.97 mmoles) was added dropwise. The reaction was deemed complete by HPLC after another 1.5 hours and water (2.11 g, 117 mmoles) was added over 10 minutes dropwise. The reaction was stirred another 5 minutes in the cold bath then placed into a refrigerator at 5° C. for overnight. The reaction was placed into an ice water bath. Triethylamine (3.25 g, 32.1 mmoles) was dissolved in dry dioxane (50 mL) and this was added slowly to the reaction mixture over 15 minutes. The reaction was stirred in the cold bath for one hour, then allowed to warm to room temperature, pH was measured at 3.0. The solid was filtered, washed with dioxane the MTBE. An oil formed in the filtrate. The isolated solid was not the desired product so enough MTBE was added to the filtrate to induce complete oiling out of the product (200 mL). The liquid was decanted from the resulting oil which was washed with MTBE (2×). The oil was treated with IPA (50 mL) and this gave a solid which was broken up with a spatula and then stirred using a magnetic stir bar for 30 minutes. This solid was isolated by filtration, washed with IPA and then MTBE and dried in vacuo to give 3.60 g of crude product, a quantitative yield. A portion of this was purified using a 40 g C-18 column using 5-30% methanol water as elution solvents giving 120 mg of purified product.

LRMS (ESI)$^+$ m/z. 614.1.

Example 11

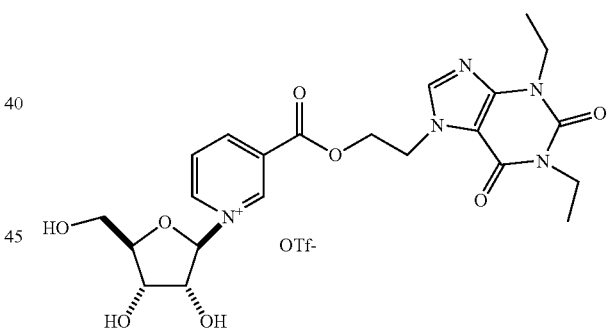

Compound 11

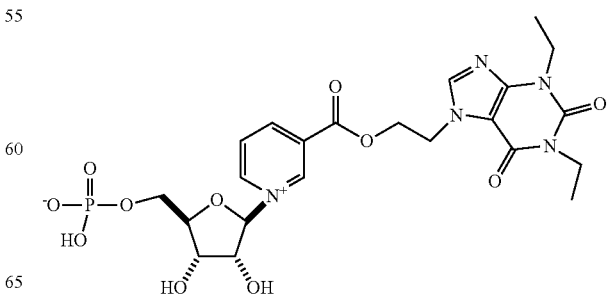

Compound 11P ((2R,3S,4R,5R)-5-(3-((2-(1,3-diethyl-2,6-dioxo-1,2,3,6-tetrahydro-7H-purin-7-yl)ethoxy)carbonyl)pyridin-1-ium-1-yl)-3,4-dihydroxytetrahydrofuran-2-yl)methyl hydrogen phosphate

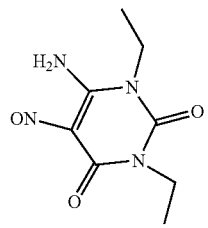

6-amino-1,3-diethyl-5-nitrosopyrimidine-2,4(1H,3H)-dione was synthesized as follows. Diethyl urea (11.6 g, 0.10 moles), cyanoacetic acid (8.50 g, 0.10 moles) and acetic anhydride (12.5 mL) were placed into a 200 mL one necked round bottomed flask with a magnetic stir bar. The flask was placed into an 80° C. oil bath and heated for 3 hours. It was removed from the oil bath and concentrated in vacuo at 50° C. The resulting oil was coevaporated with toluene (4×) giving a thick, clear oil. A solution of 5% sodium hydroxide (50 mL) was added to the oil, an exotherm developed and a thick precipitate formed. After 30 minutes, the reaction was placed into an ice water bath for 15 minutes. Sodium nitrite (8.30 g, moles) was dissolved in water (50 mL). Water (25 mL) was added to the thick reaction mixture to be able to stir the mixture. The sodium nitrite solution was added to the thick reaction mixture. Acetic acid (12.59 g, 0.21 moles) was added dropwise to the reaction. The reaction was transferred to a 500 mL round bottomed flask and water (300 mL) was added to aid in stirring. The reaction was allowed to stir overnight at room temperature. It was placed into an ice water bath for 30 minutes then filtered and the solid washed with water, a small amount of ethanol, then MTBE. The product was dried in vacuo, giving 16.92 g of a dark purple solid.

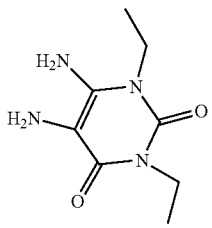

5,6-diamino-1,3-diethylpyrimidine-2,4(1H,3H)-dione was synthesized as follows. 6-amino-1,3-diethyl-5-nitrosopyrimidine-2,4(1H,3H)-dione (16.9 g, 79.7 mmoles) was added to a 500 mL one necked round bottomed flask with a magnetic stir bar. Concentrated ammonium hydroxide (85 mL) was added and this was placed into a warm water bath to bring the temperature to 35° C. Sodium hydrosulfite (46.5 g, 267 mmoles) was dissolved in water (211 mL). This solution was added over a 20 minute period to the stirred solution of the substrate, the reaction was then heated to near reflux for 20 minutes. After one hour, the reaction mixture was concentrated in vacuo at 30° C. until a large amount of solid formed. The reaction mixture was cooled in an ice water bath for 20 minutes then filtered. The solid was washed with cold water then MTBE. Drying under high vacuum gave 15.82 g of product.

LRMS (ESI)+ m/z. 199.1.

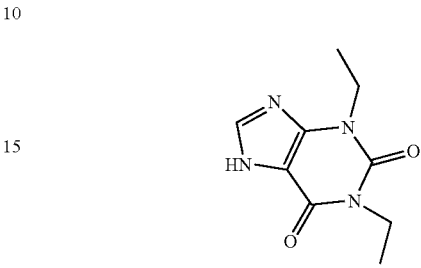

1,3-diethyl-3,7-dihydro-1H-purine-2,6-dione was synthesized as follows. 5,6-diamino-1,3-diethylpyrimidine-2,4(1H,3H)-dione (4.00 g, 20.2 mmoles) was added to a 100 mL one necked round bottomed flask with a magnetic stir bar and placed under argon. Dry DMF (20 mL) was added via syringe, then trimethylorthoformate (40 mL) was added. This solution was stirred and placed into a 95° C. oil bath overnight. It was concentrated in vacuo and the resulting solid recrystallized from water-isopropanol. This gave 2.25 g, a 53.6% yield.

LRMS (ESI)+ m/z. 209.

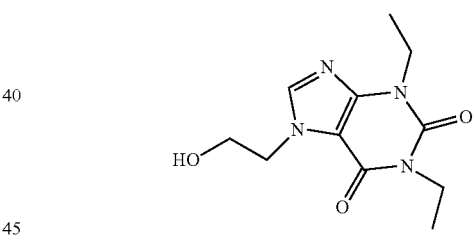

1,3-diethyl-7-(2-hydroxyethyl)-3,7-dihydro-1H-purine-2,6-dione was synthesized as follows. 1,3-diethyl-3,7-dihydro-1H-purine-2,6-dione (5.20 g, 25.0 mmoles) and potassium carbonate (crushed, 3.63 g, 26.3 mmoles) and a magnetic stir bar were placed into a 200 mL one necked round bottomed flask and put under argon. Dry DMF (70 mL) was added via syringe and he stirred solution was heated in a 120° C. oil bath for 1 hour. The reaction was removed from the oil bath and allowed to cool for 15 minutes. 2-chloroethanol (2.22 g, 26.3 mmoles) was added to the reaction using a syringe over 5 minutes. The reaction was stirred for 10 minutes then put back into the hot oil bath for one hour. It was hot filtered and the filtrate concentrated in vacuo. It was co evaporated with methanol then acetonitrile and the resulting solid was washed with MTBE to give 5.50 g, an 87.3% yield.

LRMS (ESI)+ m/z. 253.

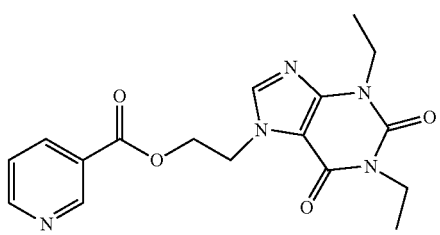 [SMILES: CCn1c(=O)c2c(ncn2CCOC(=O)c2cccnc2)n(CC)c1=O]

2-(1,3-diethyl-2,6-dioxo-1,2,3,6-tetrahydro-7H-purin-7-yl)ethyl nicotinate was synthesized as follows. 1,3-di ethyl-7-(2-hydroxyethyl)-3,7-dihydro-1H-purine-2,6-di one (1.26 g, 5.00 mmoles), nicotinic acid (0.646 g, 5.25 mmoles), 3-(3-Dimethylaminopropyl)-1-ethyl-carbodiimide hydrochloride (1.06 g, 5.53 mmoles) and dimethylaminopyridine (0.122 g, 1.00 mmoles) were combined in a 100 mL one necked round bottomed flask with a magnetic stir bar and placed under argon. DCM (20 mL) was added via syringe and the reaction was stirred. After stirring overnight the reaction was washed with saturated sodium bicarbonate solution (3×30 mL). The layers were separated and the organic phase dried over sodium sulfate. The solution was decanted and concentrated in vacuo to give a tan foam, 1.71 g, a 95.5% yield.

LRMS (ESI)+ m/z. 358.

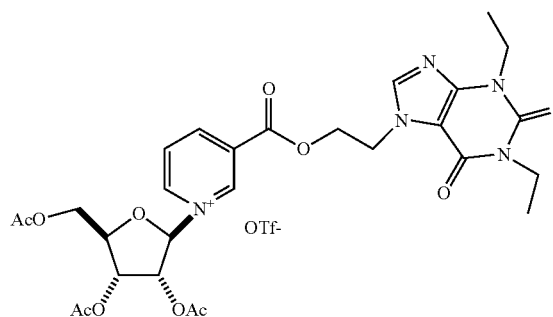

1-02R,3R,4R,5R)-3,4-diacetoxy-5-(acetoxymethyl)tetrahydrofuran-2-yl)-3-((2-(1,3-diethyl-2,6-dioxo-1,2,3,6-tetrahydro-7H-purin-7-yl)ethoxy)carbonyl)pyridin-1-ium Trifluoromethanesulfonate was synthesized as follows. 2-(1,3-diethyl-2,6-dioxo-1,2,3,6-tetrahydro-7H-purin-7-yl)ethyl nicotinate (1.71 g, 4.79 mmoles) and 1,2,3,5-Tetraacetyl-b-D-ribofuranose (1.60 g, 5.03 mmoles) were added to a 100 mL one necked round bottomed flask along with a magnetic stir bar. DCM (20 mL) was added and the reaction degassed and placed under argon. Trimethylsilyltrifluoromethane sulfonate (1.17 g, 5.27 mmoles) was added dropwise over 2 minutes. After 7 hours and 20 minutes the reaction was worked up by adding saturated sodium bicarbonate (20 mL) and the biphasic solution stirred for 10 minutes. The phases were separated and the process repeated. The organic phase was dried over sodium sulfate, decanted and concentrated in vacuo to give 3.66 g of product, a quantitative yield.

LRMS (ESI)+ m/z. 616.2

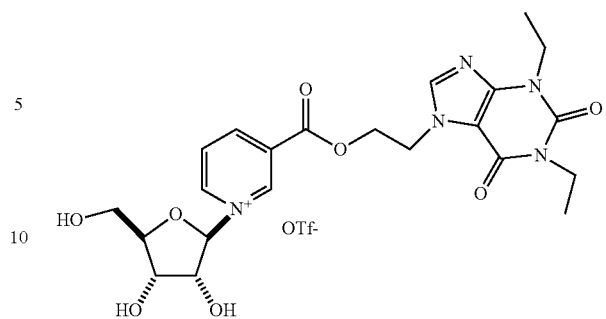

3-((2-(1,3-diethyl-2,6-dioxo-1,2,3,6-tetrahydro-7H-purin-7-yl)ethoxy)carbonyl)-1-((2R,3R,4S,5R)-3,4-dihydroxy-5-(hydroxymethyl)tetrahydrofuran-2-yl)pyridin-1-ium Trifluoromethanesulfonate was synthesized as follows. 1-((2R,3R,4R,5R)-3,4-diacetoxy-5-(acetoxymethyl)tetrahydrofuran-2-yl)-3-((2-(1,3-diethyl-2,6-dioxo-1,2,3,6-tetrahydro-7H-purin-7-yl)ethoxy)carbonyl)pyridin-1-ium Trifluoromethanesulfonate (3.66 g, 4.79 mmoles) was deprotected as described herein to give 2.68 g of product, an 87.6% yield.

LRMS (ESI)+ m/z. 490.2.

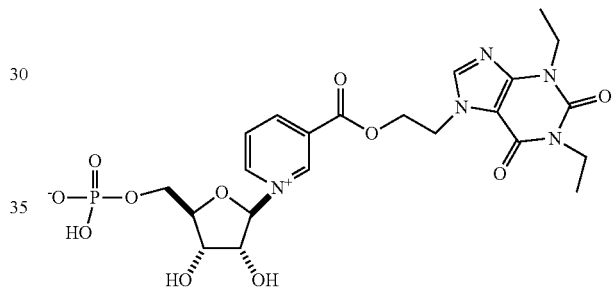

((2R,3S,4R,5R)-5-(3-((2-(1,3-diethyl-2,6-dioxo-1,2,3,6-tetrahydro-7H-purin-7-yl)ethoxy)carbonyl)pyridin-1-ium-1-yl)-3,4-dihydroxytetrahydrofuran-2-yl)methyl hydrogen phosphate was synthesized as follows. 3-((2-(1,3-diethyl-2,6-dioxo-1,2,3,6-tetrahydro-7H-purin-7-yl)ethoxy)carbonyl)-1-((2R,3R,4 S,5R)-3,4-dihydroxy-5-(hydroxymethyl) tetrahydrofuran-2-yl)pyridin-1-ium Trifluoromethanesulfonate (1.00 g, 1.57 mmoles) was phosphorylated using the procedure described herein to give 436 mg of crude product. This was purified utilizing a 40 g C-18 column and a gradient of 5-30% methanol water as eluent.

LRMS (ESI)+ m/z. 569.5.

Example B1: Biological Testing

Figure 1:
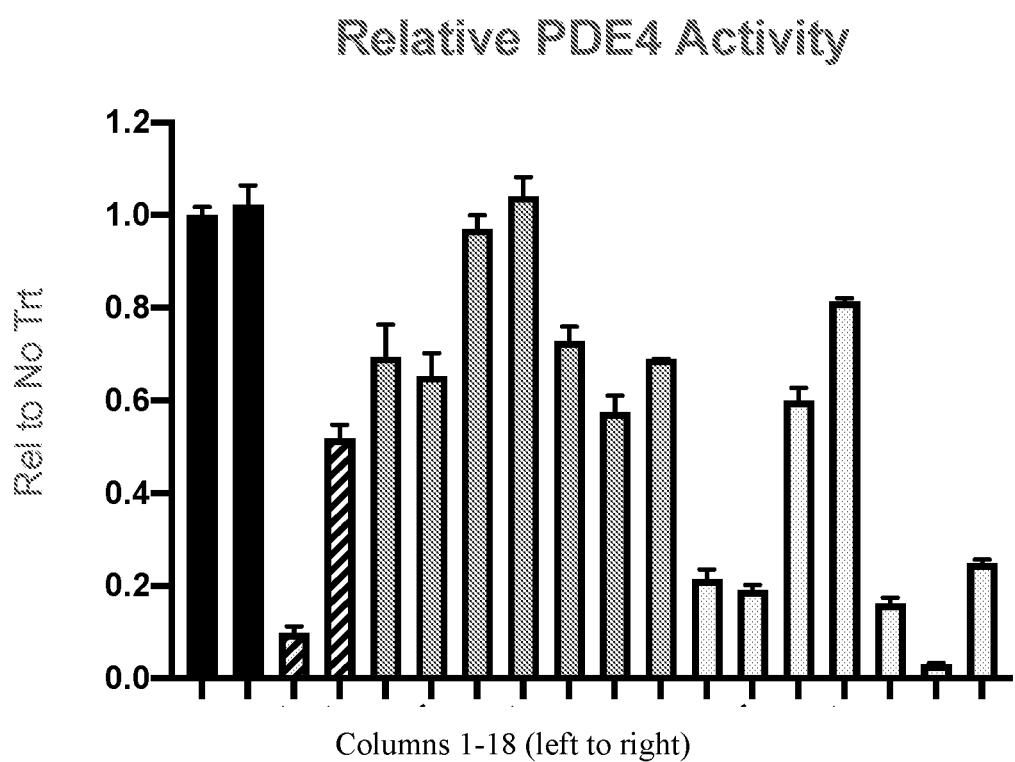
FIG. 1 provides results from studies performed to evaluate specificity of PDE4 inhibition by compounds as fully described in Example B1. The Y-axis provides relative PDE4 activity relative to no treatment (No inhibitor=1.0 in the relative scale). IBMX is 3-isobutyl-1,7-bismethyl-xanthine. RLPM is rolipram. NRCl is nicotinamide riboside chloride.

Studies were performed to evaluate specificity of PDE4 inhibition by compounds as described herein. Results are presented in FIG. 1.

Columns 1-4 Controls: 1) No inhibitor, 2) water, 3) RLPM 60 micromolar, 4) IBMX micromolar. Columns 5-11 at 0.6 mM: 5) theophylline, 6) caffeine, 7) comparative compound, 8) NRCl, 9) Compound 3, 10) Compound 1, 11) Compound 6. Columns 12-18 at 6 mM: 12) theophylline, 13) caffeine, 14) comparative compound, 15) NRCl, 16) Compound 3, 17) Compound 1, 18) Compound 6.

IBMX is 3-isobutyl-1,7-bismethyl-xanthine. RLPM is rolipram. NRCl is nicotinamide riboside chloride. "No TRT" stands for no treatment.

Additional targets for enzymatic inhibition include PDE1A1, PDE4A4B, and PDE5A1 at concentrations ranging from 0.4 mM to 10 mM.

Example B2: Biological Testing

Cisplatin-induced acute kidney injury (AKI) is an acceptable model because it is rapid (72 hours), reproducible, similar to human disease, and responsive to supplementation with nicotinamide or NMN. The study design was 48 male C57BL/6 mice randomized to six treatment groups (1-6) and subjected to cisplatin-induced AKI (25 mg/kg intraperitoneal administered cisplatin on day 0) as per Tran et al., "PGC1α drives NAD biosynthesis linking oxidative metabolism to renal protection." Nature, 24 Mar. 2016, vol 531, pages 528-532). Comparative and test compounds were administered by gavage 24 hours before injury and again at the time of injury, based on the protocol of Tran et al. Results are shown in FIG. 2. Readouts from the testing were (a) biliary urinary nitrogen (BUN), (b) serum creatinine (Cr), (c) histopathology of kidney sections viewed and graded for tubular necrosis, and (d) NAD concentration in the kidney. In each of (a)-(d), Column 1 was cisplatin alone, Column 2 was niacinamide (Nam), Column 3 was nicotinamide mononucleotide (NMN), and Column 4 was Compound 4.

Example B3: Biological Testing

Compounds were tested in an NAD Cellular Assay according to the following protocol. Jurkat cells (50,000 per in 100 microliters of RPMI media) were added to wells of a 96 well, conical bottomed plate. The cells were allowed to recover for 3 h in culture. A 16 microliter aliquot of a 100 mM compound stock solution was diluted with 784 microliters of medium and 10% FBS to give 800 microliters of a 2 mM compound treatment solution. The compound treatment solution was added to the cells for a final concentration of 1 mM compound (n=6 wells for each compound.) As a parallel control, nicotinamide mononucleotide (NMN) was added to cells at a final concentration of 2 mM (n=6). The plates were incubated for 24 hours, then spun at 1000 rpm for 10 min. The medium was removed, then the cells were washed with fresh PBS and spun again. The PBS medium was removed, then the cells were washed one more time with PBS and spun. The liquid was removed from each well via pipette, avoiding touching the cell pellet. The cells were lysed with 75 microliters of 0.5% DTAB. 25 microliters of the lysate was added to each of two flat bottomed plates. One plate was used for a BCA protein assay (clear), and the other plate was used for the NAD assay (clear bottom, white walled). The NAD concentration in each well was determined using a commercially available assay according to the kit instructions (e.g. Promega NAD/NADH-Glo™ Assay.) The Pierce BCA protein assay was run according to the kit instructions (e.g. ThermoScientific Catalog number 23225). NAD levels were normalized to total protein and reported as a multiple of the NAD level in untreated cells.

Assays with other cell types were run similarly, using the appropriate compound and NMN dilutions. Cell counts were adjusted as necessary to provide a signal within the reading range of the protein and NAD assay kits.

NAD Elevation Assay results are provided in the following Table:

| Compound | NAD Elevation Assay | Cell type |
| --- | --- | --- |
| 1 | Active at 0.4-2 mM | AML12 Cells |
| 2 | 2.9× @ 1 mM | Jurkat cells |
| 2P | 1.6× @ 2 mM | HEPG2 Cells |
| 3 | Active at 0.4-2 mM | AML12 Cells |
| 4 | 2.1× @ 0.1 mM | HEPG2 cells |
| 5P | 2.2× @ 0.25 mM | NDF Cells |
| 6P | 2.0× @ 0.25 mM | NDF cells |
| 7P | 1.9× @ 0.25 mM | NDF cells |
| 8P | 1.9× @ 0.25 mM | NDF Cells |
| 9P | 1.9× @ 0.25 mM | HEPG2 cells |
| 10P | 1.3× @ 2 mM | HEPG2 cells |
| 11P | 1.3× @ 2 mM | HEPG2 cells |

INCORPORATION BY REFERENCE

All US patents and US and PCT published patent applications and non-patent literature mentioned in this specification are herein incorporated by reference to the same extent as if each independent patent and publication was specifically and individually indicated to be incorporated by reference.

EQUIVALENTS

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

We claim:

1. A compound having a structure represented by Formula (I):

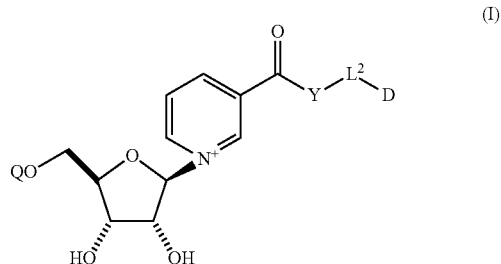

or a pharmaceutically acceptable salt thereof, wherein
(i) Q is H or —PO(OH)$_2$ or —PO(OH)(O$^-$);
(ii) Y is —NH— or —O—;
(iii) L$^2$ is
(a) (C1-6)alkylene or
(b)

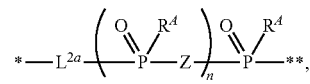

wherein
L²ᵃ is (C1-C6)alkylene;
each R⁴ is independently OH, O⁻, O-alkyl, NH-alkyl, or alkyl;
Z is O or NH;
n is 0 or 1;
* is the point of attachment to Y;
** is the point of attachment to D; and
(iv) D is an optionally substituted xanthine.

2. The compound of claim 1, wherein Y is —O—.
3. The compound of claim 1, wherein Y is —NH—.
4. The compound of claim 1, wherein L² is (C₁₋₆)alkylene.
5. The compound of claim 1, wherein L² is (C₁₋₃)alkylene.
6. The compound of claim 1, wherein Y is —O— and L² is (C₁₋₆)alkylene.
7. The compound of claim 1, wherein Y is —O— and L² is (C₂)alkylene.
8. The compound of claim 1, wherein D is a substituted xanthine.
9. The compound of claim 1, wherein D is a methylxanthine.
10. The compound of claim 1, wherein D is selected from caffeine, theobromine, and theophylline.
11. The compound of claim 1, wherein D is theobromine.
12. The compound of claim 1, wherein D is represented by Formula (III):

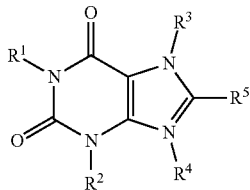

(III)

wherein
each R¹, R², R³, and R⁴ is independently (i) absent; (ii) H; (iii) (C₂₋₆)alkenyl, (C₂₋₆)alkynyl, (C₃₋₇)cycloalkyl, aryl, heteroaryl, —C(=O)(C₁₋₆)alkyl, C(=O)(O)(C₁₋₆)alkyl, (O)C(=O)(C₁₋₆)alkyl, (C₁₋₆)alkyl(O)C(=O)(C₁₋₆)alkyl, with or without a point of attachment to L²; or (iv) the point of attachment to L²;
provided that one of R¹, R², R³, and R⁴ includes the point of attachment to L²; and further provided that when R⁴ is not absent, the nitrogen to which it is attached bears a positive charge;
R⁵ is H, (C₂₋₆)alkenyl, (C₂₋₆)alkynyl, (C₃₋₇)cycloalkyl, aryl, heteroaryl, or NR⁶R⁷; and
each R⁶ and R⁷ is independently H, (C₂₋₆)alkenyl, (C₂₋₆)alkynyl, or aryl.

13. The compound of claim 1, wherein D is represented by Formula (III):

(III)

wherein
each R¹, R², R³, and R⁴ is independently (i) absent; (ii) H; (iii) (C₂₋₆)alkenyl, (C₂₋₆)alkynyl, (C₃₋₇)cycloalkyl, aryl, or heteroaryl, with or without a point of attachment to L²; or (iv) the point of attachment to L²;
provided that one of R¹, R², R³, and R⁴ includes the point of attachment to L 2; and further provided that when R⁴ is not absent, the nitrogen to which it is attached bears a positive charge;
R⁵ is H, (C₂₋₆)alkenyl, (C₂₋₆)alkynyl, (C₃₋₇)cycloalkyl, aryl, heteroaryl, or NR⁶R⁷; and
each R⁶ and R⁷ is independently H, (C₂₋₆)alkenyl, (C₂₋₆)alkynyl, or aryl.

14. The compound of claim 1, having the structure of one of the following:

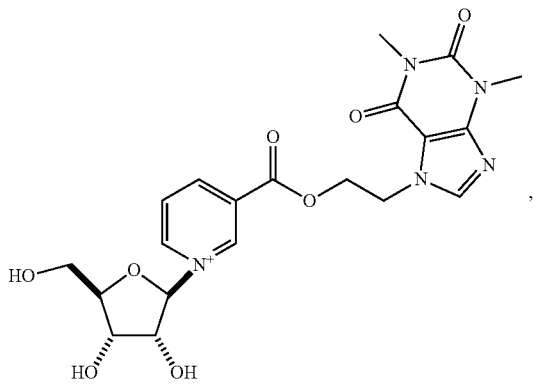

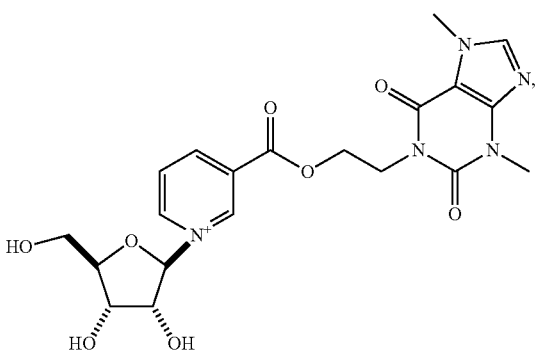

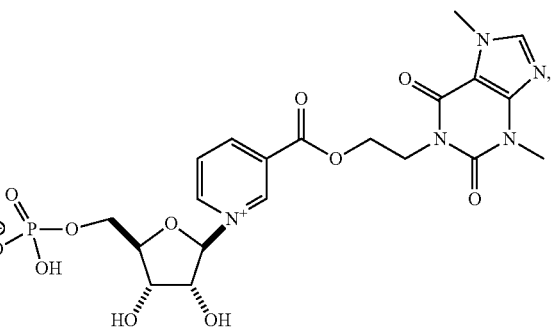

65
-continued
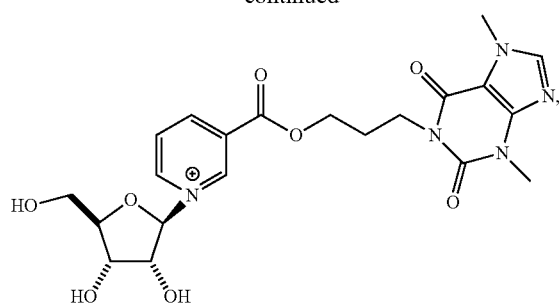
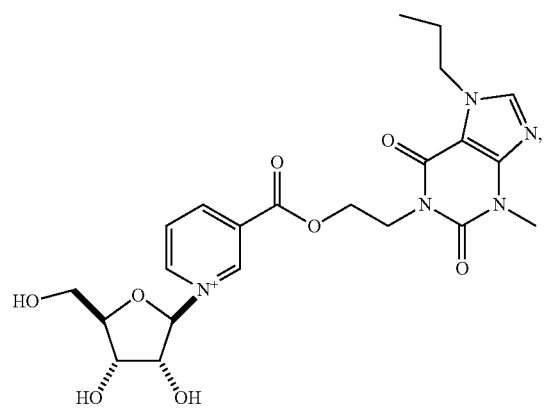
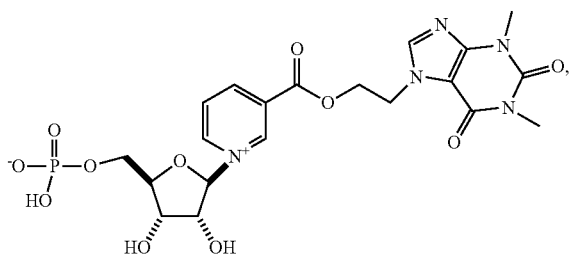
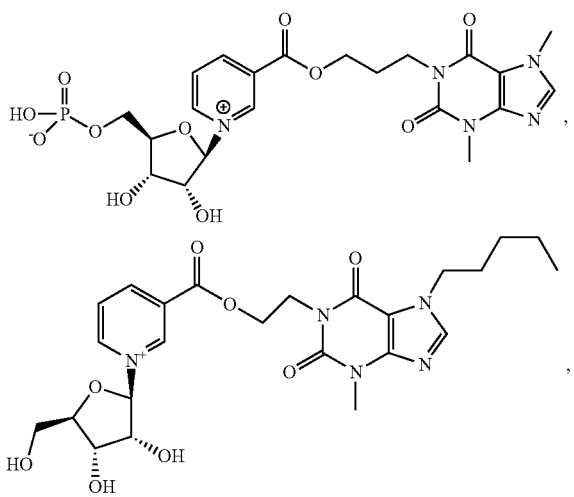
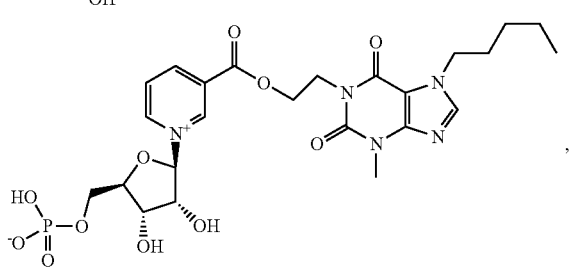
66
-continued
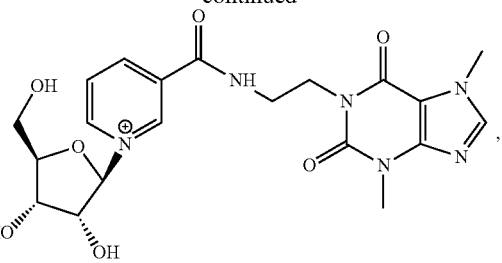
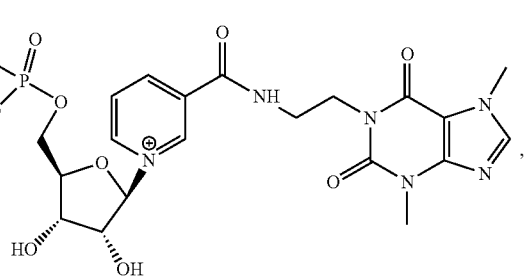
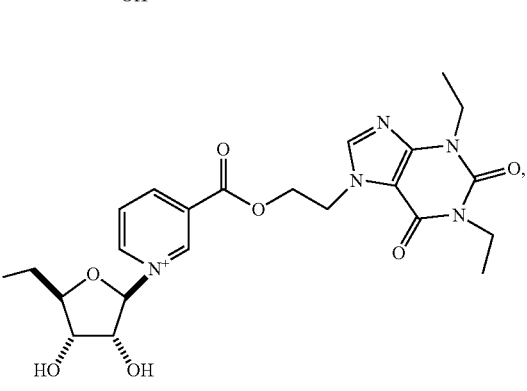
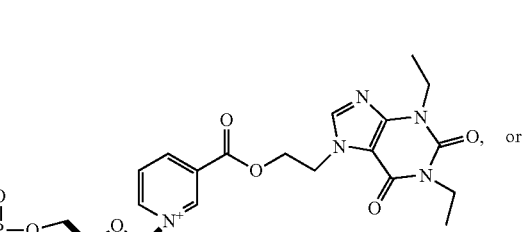
or a pharmaceutically acceptable salt thereof.

15. The compound of claim 1, having the structure of one of the following:

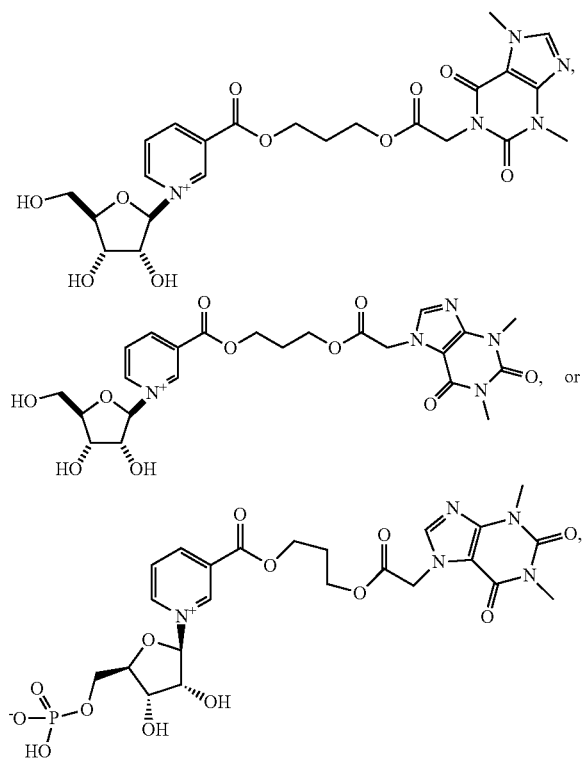

or a pharmaceutically acceptable salt thereof.

16. The compound of claim 1, having the structure of one of the following:

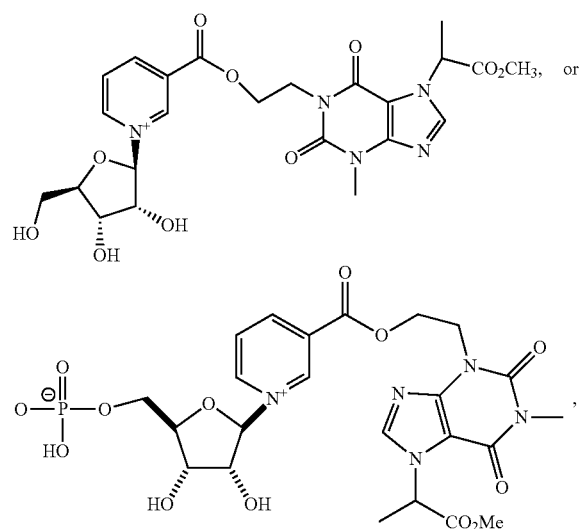

or a pharmaceutically acceptable salt thereof.

17. The compound of claim 1, having the following structure:

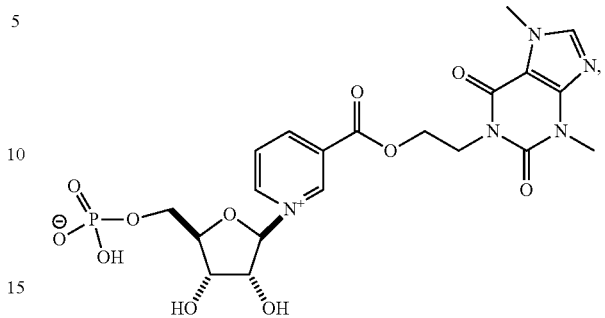

18. A pharmaceutically acceptable salt of a compound of claim 1, wherein the salt comprises a cation selected from $H^+$, $Li^+$, $Na^+$, $K^+$, $Mg^{2+}$, and $Ca^{2+}$.

19. A pharmaceutically acceptable salt of a compound of claim 1, wherein the salt comprises an anion selected from acetate, triflate, halide, trifluoroacetate, formate, $H_2PO_4^-$, $HPO_4^{2-}$, $OH^-$, $HSO_4^-$, $SO_4^{2-}$, $NO_3^-$, $HCO_3^-$, and $CO_3^{2-}$.

20. A pharmaceutical composition comprising a compound or pharmaceutically acceptable salt of claim 1 and one or more pharmaceutically acceptable excipients.

21. The pharmaceutical composition of claim 20, wherein the pharmaceutically acceptable excipient is selected from an anti-adherent, a binder, a coating, a dye, a disintegrant, a flavoring agent, a glidant, a lubricant, a preservative, a sorbent, a sweetener, a dispersant, a diluent, a filler, a granulating agent, a coating agent, a wax, a suspending agent, a wetting agent, a vehicle, a liquid carrier, and combinations thereof.

22. The pharmaceutical composition of claim 20, wherein the composition is in a solid form selected from a tablet, a pill, a capsule, a caplet, a troche, granules, powders, a sachet, a dry powder inhalation form, a chewable, a pastille, and a lozenge.

23. The pharmaceutical composition of claim 20, wherein the composition is in a solid form selected from a tablet, a pill, a capsule, and a caplet.

24. A method of treating inflammation in a subject, said method comprising administering a compound or pharmaceutically acceptable salt of claim 1 to the subject.

25. The method of claim 24, wherein the subject is human.

26. The method of claim 24, wherein the inflammation is a symptom of or a cause of asthma, chronic obstructive pulmonary disease (COPD), psoriasis, atopic dermatitis, inflammatory bowel disease (IBD), rheumatoid arthritis (RA), lupus, acute kidney injury (AKI), chronic kidney disease, or neuroinflammation.

27. A method of increasing NAD+ in a subject, said method comprising administering a compound or pharmaceutically acceptable salt of claim 1 to the subject.

28. The method of claim 27, wherein the subject is human.

29. A method of treating inflammation and increasing NAD+ in a subject, said method comprising administering a compound or pharmaceutically acceptable salt of claim 1 to the subject.

30. The method of claim 29, wherein the subject is human.

* * * * *

UNITED STATES PATENT AND TRADEMARK OFFICE
CERTIFICATE OF CORRECTION

PATENT NO. : 11,878,994 B1
APPLICATION NO. : 18/368257
DATED : January 23, 2024
INVENTOR(S) : James M. McKearin et al.

It is certified that error appears in the above-identified patent and that said Letters Patent is hereby corrected as shown below:

In the Claims

At Column 63, Claim number 12, Line number 40, please delete:
"H; (iii) $(C_{2-6})$alkenyl, $(C_{2-6})$alkynyl, $(C_{3-7})$cycloal-"
And replace with:
-- H; (iii) $(C_{1-6})$alkyl, $(C_{2-6})$alkenyl, $(C_{2-6})$alkynyl, $(C_{3-7})$cycloal- --

At Column 63, Claim number 12, Line number 50, please delete:
"$R^5$ is H, $(C_{2-6})$alkenyl, $(C_{2-6})$alkynyl, $(C_{3-7})$cycloalkyl,"
And replace with:
-- $R^5$ is H, $(C_{1-6})$alkyl, $(C_{2-6})$alkenyl, $(C_{2-6})$alkynyl, $(C_{3-7})$cycloalkyl, --

At Column 63, Claim number 12, Line number 52, please delete:
"each $R^6$ and $R^7$ is independently H, $(C_{2-6})$alkenyl,"
And replace with:
-- each $R^6$ and $R^7$ is independently H, $(C_{1-6})$alkyl, $(C_{2-6})$alkenyl, --

At Column 64, Claim number 13, Line number 3, please delete:
"H; (iii) $(C_{2-6})$alkenyl, $(C_{2-6})$alkynyl, $(C_{3-7})$cycloal-"
And replace with:
-- H; (iii) $(C_{1-6})$alkyl, $(C_{2-6})$alkenyl, $(C_{2-6})$alkynyl, $(C_{3-7})$cycloal- --

At Column 64, Claim number 13, Line number 12, please delete:
"$R^5$ is H, $(C_{2-6})$alkenyl, $(C_{2-6})$alkynyl, $(C_{3-7})$cycloalkyl,"
And replace with:
-- $R^5$ is H, $(C_{1-6})$alkyl, $(C_{2-6})$alkenyl, $(C_{2-6})$alkynyl, $(C_{3-7})$cycloalkyl, --

Signed and Sealed this
Seventh Day of May, 2024

*Katherine Kelly Vidal*
Katherine Kelly Vidal
*Director of the United States Patent and Trademark Office*

CERTIFICATE OF CORRECTION (continued)
U.S. Pat. No. 11,878,994 B1

At Column 64, Claim number 13, Line number 14, please delete:
"each $R^6$ and $R^7$ is independently H, $(C_{2-6})$alkenyl,"
And replace with:
-- each $R^6$ and $R^7$ is independently H, $(C_{1-6})$alkyl, $(C_{2-6})$alkenyl, --